(12) United States Patent
Schwarz

(10) Patent No.: US 10,470,459 B2
(45) Date of Patent: Nov. 12, 2019

(54) ANTIMICROBIAL PREPARATIONS, METHODS FOR PREPARING THE SAME AND USES THEREOF TO COMBAT MICROORGANISMS

(71) Applicant: IPABC LTD, Daventry Northamptonshire (GB)

(72) Inventor: Ulrich W. Schwarz, Daventry Northamptonshire (GB)

(73) Assignee: IPABC LTD, Daventry Northamptonshire (GB)

( * ) Notice: Subject to any disclaimer, the term of this patent is extended or adjusted under 35 U.S.C. 154(b) by 0 days.

(21) Appl. No.: 15/314,248

(22) PCT Filed: May 28, 2015

(86) PCT No.: PCT/GB2015/051560
§ 371 (c)(1),
(2) Date: Nov. 28, 2016

(87) PCT Pub. No.: WO2015/181558
PCT Pub. Date: Dec. 3, 2015

(65) Prior Publication Data
US 2017/0150714 A1 Jun. 1, 2017

(30) Foreign Application Priority Data

May 28, 2014 (GB) .................... 1409451.0

(51) Int. Cl.
| | | |
|---|---|---|
| *A01N 25/30* | (2006.01) | |
| *A61K 9/00* | (2006.01) | |
| *A61K 38/02* | (2006.01) | |
| *A61K 47/26* | (2006.01) | |
| *A61K 31/7048* | (2006.01) | |
| *A61K 45/06* | (2006.01) | |
| *A01N 25/04* | (2006.01) | |
| *A01N 37/46* | (2006.01) | |
| *A61K 9/107* | (2006.01) | |
| *A61K 9/14* | (2006.01) | |
| *A01N 25/02* | (2006.01) | |
| *A01N 37/44* | (2006.01) | |
| *A01N 47/44* | (2006.01) | |
| *A01N 63/00* | (2006.01) | |
| *A61K 9/08* | (2006.01) | |
| *A61K 31/155* | (2006.01) | |
| *A61K 38/47* | (2006.01) | |

(52) U.S. Cl.
CPC ............ *A01N 25/30* (2013.01); *A01N 25/02* (2013.01); *A01N 25/04* (2013.01); *A01N 37/44* (2013.01); *A01N 37/46* (2013.01); *A01N 47/44* (2013.01); *A01N 63/00* (2013.01); *A61K 9/0095* (2013.01); *A61K 9/08* (2013.01); *A61K 9/107* (2013.01); *A61K 9/1075* (2013.01); *A61K 9/145* (2013.01); *A61K 9/146* (2013.01); *A61K 31/155* (2013.01); *A61K 31/7048* (2013.01); *A61K 38/02* (2013.01); *A61K 38/47* (2013.01); *A61K 45/06* (2013.01); *A61K 47/26* (2013.01); *C12Y 302/01017* (2013.01)

(58) Field of Classification Search
CPC ...... A61K 38/13; A61K 47/26; A61K 8/0241; A61K 31/00; A61K 38/00; A61K 6/0067; A61K 8/0216; A01N 25/30
See application file for complete search history.

(56) References Cited

U.S. PATENT DOCUMENTS

| | | |
|---|---|---|
| 4,699,882 A | 10/1987 | Visuri |
| 4,748,158 A | 5/1988 | Biermann et al. |
| 5,120,650 A | 6/1992 | Visuri |
| 5,296,597 A * | 3/1994 | Bruzzese ............... C07H 17/08 424/122 |
| 5,681,949 A | 10/1997 | Johansson et al. |
| 5,811,280 A | 9/1998 | Visuri |
| 5,821,233 A | 10/1998 | Van Rijn et al. |
| 5,900,363 A | 5/1999 | Hiraki et al. |
| 6,531,573 B1 | 3/2003 | Oppenheim et al. |
| 6,559,281 B1 | 5/2003 | Jaynes |
| 6,855,801 B1 | 2/2005 | San Antonio et al. |

(Continued)

FOREIGN PATENT DOCUMENTS

| | | |
|---|---|---|
| CN | 101797071 A | 8/2010 |
| CN | 101940225 | 1/2011 |

(Continued)

OTHER PUBLICATIONS

Octyl-beta-Glucoside Detergent, Thermo Fisher Scientific, product specification of catalog No. 28310, accessed online on Aug. 1, 2018. (Year: 2018).*

(Continued)

Primary Examiner — Kaipeen E Yang
(74) Attorney, Agent, or Firm — Cantor Colburn LLP

(57) ABSTRACT

The present invention provides antimicrobial preparations of crystalline particles of an antimicrobial agent, wherein said antimicrobial agent is an antimicrobial peptide or an antimicrobial polyene, methods for preparing the same and uses thereof to combat microorganisms. The invention further provides crystalline particles of the antimicrobial agent so obtained from the methods of the invention in isolated form and concentrated liquid preparations which comprise said crystalline particles. The invention still further provides the use of such isolated crystalline particles and concentrated liquid preparations to combat microorganisms.

24 Claims, 3 Drawing Sheets

(56) References Cited

U.S. PATENT DOCUMENTS

| | | |
|---|---|---|
| 6,890,900 B2 | 5/2005 | Braun et al. |
| 7,015,041 B2 | 3/2006 | Santarsiero et al. |
| 7,214,540 B2 | 5/2007 | DeLucas et al. |
| 7,232,800 B2 | 6/2007 | Sun et al. |
| 7,247,203 B2 | 7/2007 | Sasaki et al. |
| 7,829,524 B2 | 11/2010 | Segura et al. |
| 7,915,223 B2 | 3/2011 | Mor et al. |
| 8,092,595 B1 | 1/2012 | Fan et al. |
| 8,097,582 B2 | 1/2012 | Grubb et al. |
| 8,252,737 B2 | 8/2012 | Hodges et al. |
| 8,367,412 B2 | 2/2013 | Yamaguchi et al. |
| 2003/0170843 A1 | 9/2003 | Margolin et al. |
| 2003/0175239 A1 | 9/2003 | Margolin et al. |
| 2005/0084471 A1 | 4/2005 | Andrews et al. |
| 2006/0083830 A1 | 4/2006 | Kemp et al. |
| 2006/0134729 A1 | 6/2006 | Besson-Faure et al. |
| 2006/0178309 A1 | 8/2006 | Visuri et al. |
| 2006/0241050 A1 | 10/2006 | Cameron et al. |
| 2008/0194689 A1 | 8/2008 | Reichwagen |
| 2009/0082443 A1 | 3/2009 | Otto et al. |
| 2009/0202557 A1 | 8/2009 | Argiriadi et al. |
| 2010/0215723 A1 | 8/2010 | Yao |
| 2011/0021415 A1 | 1/2011 | O'Neil |
| 2011/0028386 A1 | 2/2011 | Hodges et al. |
| 2011/0237499 A1 | 9/2011 | Vazquez Sentis et al. |
| 2011/0305763 A1 | 12/2011 | O'Sullivan et al. |
| 2012/0065269 A1 | 3/2012 | Ibrahim et al. |
| 2012/0251699 A1 | 10/2012 | McClements et al. |
| 2012/0258047 A1 | 10/2012 | Martoni et al. |

FOREIGN PATENT DOCUMENTS

| | | |
|---|---|---|
| DE | 2236201 A1 | 2/1973 |
| DE | 69226064 T2 | 10/1998 |
| DE | 602005004380 T2 | 7/2008 |
| DE | 102011077075 A1 | 12/2012 |
| EP | 0254419 B1 | 1/1988 |
| EP | 0256423 B1 | 4/1993 |
| EP | 0557954 B1 | 1/1999 |
| EP | 0722327 B1 | 11/2000 |
| EP | 0884058 B1 | 7/2003 |
| EP | 1477512 A1 | 11/2004 |
| EP | 1604647 A1 | 12/2005 |
| EP | 1477512 B1 | 7/2007 |
| EP | 1711511 B1 | 1/2008 |
| EP | 1709069 B1 | 1/2009 |
| EP | 2422776 A1 | 2/2012 |
| EP | 2535040 A2 | 12/2012 |
| GB | 709927 | 6/1954 |
| GB | 733740 | 7/1955 |
| GB | 835638 | 5/1960 |
| GB | 2212810 A | 8/1989 |
| IL | 103706 A | 4/1997 |
| WO | 199509638 A1 | 4/1995 |
| WO | 19990043343 A1 | 9/1999 |
| WO | 2003077882 A2 | 9/2003 |
| WO | 2004012841 A1 | 2/2004 |
| WO | 2004024753 A1 | 3/2004 |
| WO | 2004060920 A1 | 7/2004 |
| WO | 2004075938 A1 | 9/2004 |
| WO | 2006044906 A1 | 4/2006 |
| WO | 2006108835 A2 | 10/2006 |
| WO | 2006117029 A1 | 11/2006 |
| WO | 2007027859 A1 | 3/2007 |
| WO | 2011009539 A1 | 1/2011 |
| WO | 2011075848 A1 | 6/2011 |
| WO | 2012167936 A2 | 12/2012 |
| WO | 2012168050 A1 | 12/2012 |

OTHER PUBLICATIONS

McPherson et al.; "The Effects of Neutral Detergents on the Crystallization of Soluble Proteins"; Journal of Crystal Growth; 76; pp. 547-553; (1986).

International Search Report and Written Opinion; International Application No. PCT/GB2015/051560; International Filing Date May 28, 2015; dated Jul. 22, 2015; 13 pages.

Stillhart et al.; "Study of Drug Supersaturation for Rational Early Formulation Screening of Surfactant/Co-Solvent Drug Delivery Systems"; Journal of Pharmacy and Pharmacology; 65, pp. 181-192; (2013).

* cited by examiner

ANTIMICROBIAL PREPARATIONS, METHODS FOR PREPARING THE SAME AND USES THEREOF TO COMBAT MICROORGANISMS

CROSS REFERENCE TO RELATED APPLICATIONS

This application is a National Stage application of PCT/GB2015/051560 filed on May 28, 2015 which claims the benefit of GB 1409451.0 filed on May 28, 2014, both of which are incorporated by reference in their entirety herein.

The present invention relates to antimicrobial preparations, methods for preparing the same and uses thereof to combat microorganisms. More specifically there is provided a method for preparing antimicrobial liquid preparations which comprise crystalline particles of an antimicrobial agent, wherein said antimicrobial agent is an antimicrobial peptide or an antimicrobial polyene. It has been found that when antimicrobial peptides or antimicrobial polyenes are combined in solution with one or more non-ionic surfactants at a concentration sufficient to form micelles of the surfactant and that mixture is then diluted sufficiently, antimicrobial crystalline particles of said peptides or polyenes are formed. As shown in the Examples, such liquid preparations have antimicrobial activity and in some instances improved antimicrobial efficacy. Accordingly, the use of such liquid preparations to combat the contamination of a site, particularly large scale industrial, agricultural and commercial sites, with a microorganism is proposed. The site may be in any context, and as such both medical and non-medical uses are provided. The invention further relates to the crystalline particles of the antimicrobial agent so obtained in isolated form and concentrated liquid preparations which comprise crystalline particles of an antimicrobial agent and the use thereof to combat microorganisms.

Antimicrobial peptides are a class of low molecular weight proteins which show a broad spectrum antimicrobial activity against bacteria, viruses, and fungi. More than 800 natural antimicrobial peptides have been isolated from a wide range of organisms, including plants, animals (including mammals) and microorganisms. Artificial antimicrobial peptides have been prepared based thereon. In accordance with the invention ε-poly-L-lysine and other substantially homogeneous peptides with amino acid residues linked via the a carbon and/or c amine and which have antimicrobial activity are considered antimicrobial peptides.

Antimicrobial peptides typically contain positively charged and hydrophobic regions, although some anionic antimicrobial peptides have been observed. Because of their hydrophobic and hydrophilic nature, antimicrobial peptides are soluble in aqueous environments but also enter lipid-rich membranes, e.g. cell membranes. Most antimicrobial peptides work directly against cellular microbes through a mechanism involving membrane disruption and pore formation, allowing efflux of essential ions and nutrients. Some antimicrobial peptides also possess anti-viral properties, e.g. by inhibiting viral fusion and egress, and thus may prevent viral infection and viral spread. The ability of antimicrobial peptides to kill conventionally multidrug resistant microorganisms has gained them considerable attention and clinical interest.

The antimicrobial agent may also be an antimicrobial polyene (e.g. a polyene antimycotic or polyene antibiotic). Polyenes are poly-unsaturated organic compounds that contain one or more sequences of alternating double and single carbon-carbon bonds and have a variety of activities, an antimicrobial activity being one. Typically, but not exclusively, antimicrobial polyene compounds target fungi. Those obtained from some species of *Streptomyces* bacteria have been well characterised and are believed to exert their antifungal activity by binding to ergosterol in the fungal cell membrane. This binding and weakens the cell membrane and allows leakage of K+ and Na+ ions, which is believed to contribute to fungal cell death. Antimicrobial polyenes include, but are not limited to amphotericin B, nystatin, natamycin, rimocidin, filipin, hamycin and perimycin.

With microbial resistance to conventional antimicrobial agents growing, the need for unconventional therapeutic options has become urgent. The provision of crystalline particles of antimicrobial peptides and antimicrobial polyenes may further improve their advantageous properties, including their antimicrobial efficacy.

Conventional methods for the crystallisation of large molecules (e.g. proteins) are based on the aggregation of such molecules at very high concentrations, i.e. at the point of supersaturation. For clarity, the following refers to the crystallisation of proteins, but the same techniques may be applied to other large water soluble molecules that may be crystallised. A solution of a protein becomes supersaturated when the concentration of the protein is brought above the solubility limit. At such concentrations the protein begins to aggregate and depending on the precise conditions involved that aggregation may be as an amorphous precipitate or as microcrystals. The aggregation of the protein follows two steps: (i) nucleation and (ii) growth. When the protein concentration is well above saturation, amorphous precipitates are predominant. When the protein concentration is brought above its saturation point too quickly, amorphous precipitates are again predominant, especially as crystals grow much slower than amorphous precipitates do. In the metastable region, if a few nuclei are present they will continue to grow forming protein crystals, but without spontaneous formation of new nuclei. Therefore, in general, the key step in conventional protein crystallisation techniques is to exceed the saturation point only slightly and as slowly as possible. Techniques referred to as sitting drop vapour diffusion, hanging drop vapour diffusion, sandwich drop, batch, microbatch under oil, microdialysis, and free interface diffusion are commonly used in crystallization experiments. Vapour diffusion (hanging drop) technique is the most frequently used crystallization method. In this method a drop containing protein, buffer, salt and precipitant and a reservoir containing buffer, salt and precipitant are prepared with differing compound concentrations. Under vapour the equilibrium between drop and reservoir is adjusted by diffusion. Within the drop the protein becomes supersaturated and crystals start to form. Free interface diffusion has been used in microgravity crystallisation trials. In this technique the protein sample is in liquid contact with the precipitant and over time the sample and precipitant diffuse into one another and crystallisation may occur at the interface. In batch crystallisation the protein sample is mixed with the precipitant and additives to form a homogenous crystallisation medium in which crystals form. In microbatch under oil a small drop of the sample plus the crystallisation agent is pipetted under a layer of oil (paraffin, silicon oils). Water vapour evaporates from the drop and as a result the sample and reagent increase in concentration. This leads to crystallisation. In dialysis crystallisation the protein sample is placed in a dialysis button and sealed with a dialysis membrane. The dialysis button is then placed into a container with crystallisation medium and water and some precipitants are then allowed to exchange while retaining the sample in the cell. As the concentration of the sample rises, crystallisation occurs. All of these options are time-consuming, difficult to master and unreliable. A simple and routine approach to the preparation of crystalline particles of antimicrobial peptides and antimicrobial polyenes would be desirous.

It has now surprisingly been found that when antimicrobial peptides or antimicrobial polyenes are combined in solution with one or more non-ionic surfactants at a concentration sufficient to form micelles of the surfactant, and that mixture is then diluted sufficiently, antimicrobial crystalline particles of said peptides or polyenes are formed.

Thus, in a first aspect the invention provides a method for preparing an antimicrobial preparation comprising crystalline particles of an antimicrobial agent, wherein said antimicrobial agent is an antimicrobial peptide or an antimicrobial polyene, said method comprising:
(i) providing an aqueous liquid composition comprising said antimicrobial agent and at least one non-ionic surfactant in solution, wherein the non-ionic surfactant is present at a concentration above the critical micelle concentration (CMC) of the non-ionic surfactant in said composition, and
(ii) diluting said aqueous liquid composition with an amount of aqueous solvent sufficient to lower the concentration of the said at least one non-ionic surfactant to a concentration at or below its CMC, thereby to result in the formation of crystalline particles of said antimicrobial agent and thereby to obtain a liquid preparation comprising said crystalline particles of said antimicrobial agent, and optionally
(iii) isolating at least a portion of said crystalline particles from said liquid preparation and/or removing at least a portion of the liquid phase of the liquid preparation to provide a more concentrated liquid preparation of crystalline particles.

The term "crystalline particles" is used herein to describe a solid particulate form that, at least in part, displays a crystal structure; that is a structure of a solid in which the constituent molecules are arranged in an ordered pattern extending in all three spatial dimensions. The crystalline particles can be of any size. The crystalline particles need not be of a size detectable by the naked eye, and so may be of a size detectable by assisted means, e.g. by microscope (e.g. electron microscope) or spectrophotometer. Accordingly, the particles may have an average diameter of at least 1 nm, e.g. at least 100 nm, 500 nm, 1 μm, 100 μm, 500 μm or 1 mm and may be referred to as crystalline nanoparticles (nanocrystals) or, crystalline microparticles (microcrystals).

In certain embodiments all, or essentially all, of the particle has a crystal structure. That crystal structure may be a single crystal or a plurality of crystals within the particle. This latter arrangement may be referred to as a polycrystal structure. As can be seen, the crystalline particles of the invention may in part have a non-crystal structure, e.g. an amphorous structure. In this regard, this non-crystal structure may arise from the presence of components in addition to the antimicrobial agent.

In accordance with the invention, the crystalline particles of an antimicrobial agent comprise an antimicrobial peptide and/or an antimicrobial polyene in crystal form. Preferably the crystal structure of the crystalline particles will be formed of, at least in part, preferably consist essentially of, the antimicrobial agent. The crystalline particles may comprise a plurality of different antimicrobial peptides and/or antimicrobial polyenes. The crystalline particles of an antimicrobial agent of the invention may also comprise components that are not an antimicrobial peptide or antimicrobial polyene and which may or may not be crystallisable, e.g. non-antimicrobial proteins, carbohydrates (e.g. saccharides, including glucose, sucrose, maltose, galactose, fructose), nucleic acids and salts. Such components might be incorporated into the particles as the crystalline particles form in accordance with the invention. In certain embodiments the crystalline particles comprise at least 10%, e.g. at least 20, 30, 40, 50, 60, 70, 80, or 90% or 100% of the antimicrobial agent of which at least 50%, e.g. at least 60, 70, 80, or 90% or 100% of the antimicrobial agent is in substantially crystal form.

In certain embodiments the particles do not further comprise an antimicrobial agent that is not an antimicrobial peptide and/or an antimicrobial polyene, e.g. an antimicrobial biguanide (e.g. polyaminopropyl biguanide (PAPB) or polyhexamethylene biguanide (PHMB) or chlorhexidine).

In certain embodiments substantially, e.g. essentially, all of the antimicrobial agent in the liquid preparation directly obtained from the dilution step (step (ii)) is in crystalline form or otherwise associated with the crystalline particles. Expressed numerically at least 60%, e.g. at least 70%, 80%, 90%, 95% or 100% of the antimicrobial agent in the liquid preparation directly obtained from the dilution step is in crystalline form or otherwise associated with the crystalline particles. In other words substantially, e.g. or essentially, none of the antimicrobial agent in the liquid preparation directly obtained from the dilution step is in solution. Expressed numerically, less than 40%, e.g. less than 30%, 20%, 10%, 5% or none of the antimicrobial agent in the liquid preparation directly obtained from the dilution step is in solution.

The term "critical micelle concentration" refers to the concentration of a surfactant in a polar solvent above which the surfactant molecules will spontaneously arrange as a micelle. In accordance with the invention, this value may be expressed in any convenient units of concentration, with the exception that when CMC values are undergoing comparison, the value is expressed as a molar concentration (i.e. in units of M, mM, μM, etc., as appropriate). In the present context a micelle is considered to be a colloid arrangement of surfactant molecules in a polar solvent in which the hydrophilic head groups are oriented towards the polar solvent in a substantially spherical shape and the hydrophobic tail groups are sequestered to the interior of the sphere. In the present context a reference to the CMC of a surfactant is a reference to the CMC of the surfactant in the conditions of the aqueous liquid composition of the invention (including physical conditions such as temperature), unless otherwise indicated. For convenience, this may be taken as the CMC of the surfactant in isolation in pure water at 20° C. CMC values may be calculated by any convenient means, preferably by one of the methods described in Mukerjee P., et. al, Critical Micelle Concentrations of Aqueous Surfactant Systems, United States Department of Commerce, Nat. Stnd. Ref. Data Ser., Nat. Bur. Stand., February 1971 (U.S.).

The dilution of the aqueous liquid composition comprising the antimicrobial agent and at least one non-ionic surfactant in solution may be achieved in a single step or a plurality of steps. The aqueous liquid composition may be added to the aqueous solvent, the aqueous solvent may be added to the aqueous liquid composition or each element may be combined simultaneously. In embodiments where a plurality of steps are employed, these may be additive/cumulative (repeated addition of aqueous solvent to the aqueous liquid composition, or portion thereof) or serial (repeated addition of the mixture of aqueous liquid composition and aqueous solvent, or portion thereof, to more solvent) or a combination thereof. Preferably dilution is achieved in less than 10 steps, e.g. less than 9, 8, 7, 6, 5, 4, or 3 steps. More preferably dilution is achieved in 2 steps or, most conveniently, a single step. Dilution, whether as a single step or the result of a plurality of steps lowers the concentration of the non-ionic surfactant in the mixture to a concentration at or, preferably, below its CMC, i.e. a concentration in the liquid preparation of step (ii) of 0.0001 to 1 times the CMC of the non-ionic surfactant, e.g. 0.0005 to 1, 0.001 to 1, 0.005 to 1, 0.01 to 1, 0.05 to 1, 0.1 to 1, 0.5 to 1, preferably 0.0001 to 0.99 times the CMC of the non-ionic surfactant, e.g. 0.0005 to 0.99, 0.001 to 0.99, 0.005 to 0.99, 0.01 to 0.99, 0.05 to 0.99, 0.1 to 0.99, 0.5 to 0.99, 0.0005 to 0.95, 0.001 to 0.95, 0.005 to 0.95, 0.01 to 0.95, 0.05 to 0.95, 0.1 to 0.95, 0.5 to 0.95, 0.001 to 0.9, 0.005 to 0.9, 0.01 to 0.9, 0.05 to 0.9, 0.1 to 0.9, 0.5 to 0.9, 0.001 to 0.8, 0.005 to 0.8, 0.01 to 0.8, 0.05 to 0.8, 0.1 to 0.8, 0.5 to 0.8, 0.001 to 0.7, 0.005 to 0.7, 0.01 to 0.7, 0.05 to 0.7, 0.1 to 0.7, 0.5 to 0.7, 0.001 to 0.6, 0.005 to 0.6, 0.01 to 0.6, 0.05 to 0.6, 0.1 to 0.6, 0.5 to 0.6, 0.001 to 0.5, 0.005 to 0.5, 0.01 to 0.5, 0.05 to 0.5, 0.1 to 0.5, 0.15 to 0.2, 0.15 to 0.25, 0.15 to 0.30, 0.15 to 0.35, 0.15 to 0.4, 0.15 to 0.45, 0.15 to 0.5, 0.2 to 0.25, 0.2 to 0.30, 0.2 to 0.35, 0.2 to 0.4, 0.2 to 0.45, 0.2 to 0.5, 0.25 to 0.30, 0.25 to 0.35, 0.25 to 0.4, 0.25 to 0.45, 0.25 to 0.5, 0.30 to 0.35, 0.3 to 0.4, 0.3 to 0.45, 0.3 to 0.5, 0.35 to 0.4, 0.35 to 0.45, 0.35 to 0.5, 0.4 to 0.45, 0.4 to 0.5 or 0.45 to 0.5 times the CMC of the non-ionic surfactant.

Step (ii) of the method of the invention may further include a step following dilution, or if a plurality of dilution steps are used, interspacing at least two of these dilution steps, of incubating the mixture of aqueous liquid composition and solvent for a time. This incubation may be performed in a container, preferably without any addition of solvent and/or aqueous liquid composition and/or mixture thereof. In other embodiments incubation may take place at the ultimate site of action of the crystalline particles, e.g. those in vivo or in vitro locations described below, e.g. following sprat application/administration. Preferably a portion of the incubation mixture is not removed in either of these embodiments. In other words, the incubation is allowed to proceed with essentially no change in composition and/or volume. Preferably the mixture is incubated for a time sufficient for a change in the turbidity of the mixture to be observed and/or detectable (e.g. visible) crystals to form. As discussed above, this may be by assisted means.

Incubation time may be at least 1 min, e.g. at least 5, 10, 15, 30, 45, 60 mins or least 1, 2, 3, 6, 12, 24 hours or at least 1, 2, 3, 4 or 5 days. Incubation may be conducted at any convenient and practical temperature, these conditions being dictated to an extent by parameters including the freezing and boiling points of the aqueous liquid composition and the aqueous solvent and the thermolability of the antimicrobial agent. Conveniently incubation may be performed at 0° C. to 60° C., e.g. 4° C. to 50° C., 4° C. to 40° C., 4° C. to 30° C., 4° C. to 20° C., 10° C. to 50° C., 10° C. to 40° C., 10° C. to 30° C., 10° C. to 20° C., 15° C. to 50° C., 15° C. to 40° C., 15° C. to 30° C., 15° C. to 20° C., 20° C. to 50° C., 20° C. to 40° C., or 20° C. to 30° C. Conveniently incubation may be performed at about room temperature (18-25° C.) or ambient temperatures. Incubation may also be performed at or about human body temperature (e.g. about 37° C., e.g. about 35, 36, 37, 38, 39 or 40° C.).

The maximum amount of the non-ionic surfactant and the amount of the antimicrobial agent in solution in the aqueous liquid composition is in theory limited only by the solubility of these components in the aqueous liquid composition because the skilled man is free to dilute the aqueous liquid composition as much as is necessary to lower the concentration of the non-ionic surfactant to a concentration at or below the CMC of the non-ionic surfactant. Nevertheless, in general it is preferred that the concentration of the antimicrobial agent and/or the non-ionic surfactant does not exceed 20% (200,000 ppm), e.g. does not exceed 15% (150,000 ppm), 10% (100,000 ppm), 5% (50,000 ppm) or 1% (10,000 ppm). The skilled man would however appreciate that of greater relevance to the invention is the relative amounts of each component, for a sufficient amount of antimicrobial agent must be present in the aqueous liquid composition to ensure that upon dilution of the aqueous liquid composition to reach a concentration of non-ionic surfactant at or below the CMC of the non-ionic surfactant, sufficient antimicrobial agent is present to form the crystalline particles and to impart an antimicrobial effect.

It will be seen that in general the antimicrobial agent will preferably be present in solution in the aqueous liquid composition in a mass concentration (which term is conveniently interchangeable with "parts-per-million" (ppm, i.e. mg of solute per liter of solution); "% w/v"; "g/100 ml"; or the like) that is about the same or essentially the same as or greater than that of the non-ionic surfactant. In that way the antimicrobial agent cannot be diluted out before the non-ionic surfactant. In these embodiments, by "about the same" it is meant a mass concentration ratio of antimicrobial agent to non-ionic surfactant of 1000:1 to 1:1000, e.g. any of 1000:1, 500:1, 250:1, 200:1, 150:1, 100:1, 50:1, 40:1, 30:1, 20:1, 10:1, 5:1, 2:1 to any of 1:2, 1:5, 1:10, 1:20, 1:30, 1:40, 1:50, 1:100, 1:150, 1:200, 1:250, 1:500, 1:1000 or 1:1. By "essentially the same" it is meant a mass concentration ratio of antimicrobial agent to non-ionic surfactant of 250:1 to 1:250, e.g. any of 250:1, 200:1, 150:1, 100:1, 50:1, 40:1, 30:1, 20:1, 10:1, 5:1, 2:1 to any of 1:2, 1:5, 1:10, 1:20, 1:30, 1:40, 1:50, 1:100, 1:150, 1:200, 1:250 or 1:1. By "the same" it is meant a mass concentration ratio of antimicrobial to non-ionic surfactant of 1.9:1 to 1:1.9, e.g. any of 1.9:1, 1.8:1, 1.7:1, 1.6:1, 1.5:1, 1.4:1, 1.3:1, 1.2:1 to any of 1:1.2, 1:1.3, 1:1.4, 1:1.5, 1:1.6, 1:1.7, 1:1.8, 1:1.9 or 1:1. In these embodiments, by "greater than" it is meant a mass concentration ratio of antimicrobial agent to non-ionic surfactant of greater than 1:1, e.g. at least 2:1, 5:1, 10:1, 20:1, 30:1, 40:1, 50:1, 100:1, 200:1, 250:1, 500:1, 1000:1, 1500:1, 2000:1, 5000:1, 10000:1, 50000:1 or 100000:1. Expressed differently "greater than" can mean a mass concentration ratio of antimicrobial agent to non-ionic surfactant of greater than 1:1 but less than 2:1, e.g. at least 1:1 but less than 5:1, 10:1, 20:1, 30:1, 40:1, 50:1, 100:1, 200:1, 250:1, 500:1, 1000:1, 1500:1, 2000:1, 5000:1, 10000:1, 50000:1 or 100000:1.

In a further embodiment, the mass concentration of the antimicrobial agent may be at least twice the mass concentration of the non-ionic surfactant, e.g. at least 3, 5, 10, 30, 40, 50, 100, 150, 200, 250, 500, 1000, 1500, 2000, 5000, 10000, 50000, or 100000 times the mass concentration of the surfactant.

In a further embodiment the mass concentration of the antimicrobial agent may be at least twice the CMC of the surfactant, when expressed as a mass concentration, e.g. at least 3, 5, 10, 30, 40, 50, 100, 150, 200, 250, 500, 1000, 1500, 2000, 5000, 10000, 50000, or 100000 times the CMC of the surfactant, when expressed as a mass concentration.

Nevertheless, in some embodiments the skilled man may choose to use a mass concentration of antimicrobial agent that is less than that of the non-ionic surfactant but sufficient to result in crystalline particles of the antimicrobial agent upon dilution. Such embodiments may be expressed as a mass concentration ratio of antimicrobial agent to non-ionic surfactant of less than 1:1, e.g. no more than 1:2, 1:5, 1:10, 1:20, 1:30, 1:40, 1:50, 1:100, 1:150, 1:200, 1:250, 1:500, 1:1000, 1:1500, 1:2000, 1:5000, 1:10000, 1:50000, or 1:100000. Expressed differently, in these embodiments, "less than" can be viewed as a mass concentration ratio of antimicrobial agent to non-ionic surfactant of less than 1:1 but greater than 1:100000, e.g. less than 1:1 but greater than 1:50000, 1:10000, 1:5000, 1:2000, 1:1500, 1:1000, 1:500, 1:250, 1:200, 1:150, 1:100, 1:50, 1:40, 1:30, 1:20, 1:10, 1:5 or 1:2

In a further embodiment, the mass concentration of non-ionic surfactant may be at least twice the mass concentration of the antimicrobial agent, e.g. at least 3, 5, 10, 30, 40, 50, 100, 150, 200, 250, 500, 1000, 1500, 2000, 5000, 10000, 50000, or 100000 times the mass concentration of the antimicrobial agent.

In a further embodiment the mass concentration of the antimicrobial agent may be less than half that of the CMC of the surfactant, when expressed as a mass concentration, e.g. less than $\frac{1}{3}$, $\frac{1}{5}$, $\frac{1}{10}$, $\frac{1}{30}$, $\frac{1}{40}$, $\frac{1}{50}$, $\frac{1}{100}$, $\frac{1}{150}$, $\frac{1}{200}$, $\frac{1}{250}$, $\frac{1}{500}$, $\frac{1}{1000}$, $\frac{1}{1500}$, $\frac{1}{2000}$, $\frac{1}{5000}$, $\frac{1}{10000}$, $\frac{1}{50000}$, or $\frac{1}{100000}$ the CMC of the surfactant, when expressed as a mass concentration.

In certain embodiments the aqueous liquid composition comprising the antimicrobial agent in solution will comprise two or more different non-ionic surfactants, e.g. at least 3, 4, or 5. In these embodiments at least one of the non-ionic surfactants, e.g. at least 2, 3, 4 or 5, or preferably all, is present at a concentration above its CMC in said aqueous liquid composition. In these embodiments at least one of, e.g. at least 2, 3, 4 or 5, or preferably all, of the non-ionic surfactants present at a concentration above its CMC will be diluted to a concentration at or below its CMC. In these embodiments the antimicrobial agent will preferably be present in solution in the aqueous liquid composition in a mass concentration that is about the same or essentially the same as or greater than that of the non-ionic surfactant (or one of the non-ionic surfactants) to be diluted to a concentration at or below its CMC. Nevertheless, in some embodiments the skilled man may choose to use a mass concentration of antimicrobial agent that is less than that of the non-ionic surfactant to be diluted to a concentration at or below its CMC, but sufficient to result in crystalline particles of the antimicrobial agent upon dilution. The above mentioned ratios of non-ionic surfactant to antimicrobial agent, and vice versa, apply to this embodiment. In other embodiments the mass concentration of the antimicrobial agent is linked, as described above, to the surfactant to be diluted to a concentration at or below its CMC that has the highest CMC. In other embodiments the mass concentration of the antimicrobial agent is linked, as described above, to the non-ionic surfactant to be diluted to a concentration at or below its CMC that has the lowest CMC. In still further embodiments the mass concentration of the antimicrobial agent is linked, as described above, to the non-ionic surfactant to be diluted to a concentration at or below its CMC that is most abundant in the aqueous liquid composition or to the total amount of all such surfactants in the aqueous liquid composition.

Any further non-ionic surfactants, e.g. those that under the dilution conditions to be applied will remain at a concentration above their CMC, may be present in any amount which does not interfere with the formation of crystalline particles in accordance with the method of the invention. Preferably such surfactants will not be present in excess to the surfactant(s) to be diluted to a concentration at or below its CMC. Expressed numerically, such surfactants will be present in the aqueous liquid composition at a concentration that, upon dilution, gives a concentration in the liquid preparation comprising crystalline particles of step (ii) of the invention which is less than a concentration which is 500 times their CMC, e.g. no more than 400, 300, 200, 100, 50, 40, 30, 20, 10, 9, 8, 7, 6, 5, 4, 3 or 2 times their CMC. Alternatively, in the aqueous liquid composition comprising the non-ionic surfactants and antimicrobial agent in solution, such surfactants will be present at a mass concentration which is no more than 500 times, e.g. no more than 400, 300, 200, 100, 50, 40, 30, 20, 10, 9, 8, 7, 6, 5, 4, 3 or 2 times, the mass concentration of the at least one of the non-ionic surfactants to be diluted to a concentration at or below its CMC, e.g. the most abundant non-ionic surfactant to be diluted to a concentration at or below its CMC in the aqueous liquid composition.

In embodiments in which two or more different non-ionic surfactants are present in the aqueous liquid composition at respective concentrations above the respective CMCs of each non-ionic surfactant, it is preferred that the dilution of the aqueous liquid composition lowers (i) the concentration of at least one of the non-ionic surfactants to a concentration at or below its CMC and (ii) the concentration of least one of the non-ionic surfactants to a concentration that is above its CMC.

For the sake of simplicity, the present multi-surfactant embodiments of the invention will be described with reference to an arrangement consisting of an antimicrobial agent and two different non-ionic surfactants. No other surfactants are present. The skilled man would be able to apply these teachings to more complex arrangements, e.g. those with greater numbers of different non-ionic surfactants. The following discussion may be applied directly to alkyl (poly) glycoside surfactants, e.g. those described below, in particular octyl- and decyl-glucosides and specifically octyl β-D-glucopyranoside or decyl β-D-glucopyranoside.

It will be seen that it is possible to put the present preferred multi-surfactant embodiment into effect in two ways depending on which of the two non-ionic surfactants is selected to be diluted to a concentration at or below its CMC (surfactant$_{belowCMC}$). The other non-ionic surfactant may be referred to as surfactant$_{aboveCMC}$.

If the selected non-ionic surfactant (surfactant$_{belowCMC}$) is the non-ionic surfactant with the higher CMC (surfactant$_{CMC-high}$) it will be preferable for the non-ionic surfactant with the lower CMC (surfactant$_{CMC-low}$) to be present in the aqueous liquid composition at a mass concentration that is about the same as, or essentially the same as, or greater than that of surfactant$_{CMC-high}$. In that way it is more convenient to effect dilution in such a way that the concentration of surfactant$_{CMC-high}$ is lowered at or below its CMC but the concentration of surfactant$_{CMC-low}$ remains above its CMC. The skilled man would immediately appreciate that the relative CMC values for the chosen surfactants will influence how similar or how different the relative mass concentrations of the non-ionic surfactants may be. As mentioned above, for the purposes of comparison between CMC values, such values should be expressed as molar concentrations (i.e. as M, mM, μM, etc., as appropriate).

In these embodiments, by "about the same" it is meant a mass concentration ratio of surfactant$_{CMC-low}$ to surfactant$_{CMC-high}$ of 1000:1 to 1:1000, e.g. any of 1000:1, 500:1, 250:1, 200:1, 150:1, 100:1, 50:1, 40:1, 30:1, 20:1, 10:1, 5:1, 2:1 to any of 1:2, 1:5, 1:10, 1:20, 1:30, 1:40, 1:50, 1:100, 1:150, 1:200, 1:250, 1:500, 1:1000 or 1:1. By "essentially the same" it is meant a mass concentration ratio surfactant$_{CMC\text{-}low}$ to surfactant$_{CMC\text{-}high}$ of 250:1 to 1:250, e.g. any of 250:1, 200:1, 150:1, 100:1, 50:1, 40:1, 30:1, 20:1, 10:1, 5:1, 2:1 to any of 1:2, 1:5, 1:10, 1:20, 1:30, 1:40, 1:50, 1:100, 1:150, 1:200, 1:250 or 1:1. By "the same" it is meant a mass concentration ratio of surfactant$_{CMC\text{-}low}$ to surfactant$_{CMC\text{-}high}$ of 1.9:1 to 1:1.9, e.g. any of 1.9:1, 1.8:1, 1.7:1, 1.6:1, 1.5:1, 1.4:1, 1.3:1, 1.2:1 to any of 1:1.2, 1:1.3, 1:1.4, 1:1.5, 1:1.6, 1:1.7, 1:1.8, 1:1.9 or 1:1. In these embodiments, by "greater than" it is meant a mass concentration ratio of surfactant$_{CMC\text{-}low}$ to surfactant$_{CMC\text{-}high}$ of greater than 1:1, e.g. at least 2:1, 5:1, 10:1, 20:1, 30:1, 40:1, 50:1, 100:1, 200:1, 250:1, 500:1, 1000:1, 1500:1, 2000:1, 5000:1, 10000:1, 50000:1 or 100000:1. Expressed differently "greater than" can mean a mass concentration ratio of surfactant$_{CMC\text{-}low}$ to surfactant$_{CMC\text{-}high}$ of greater than 1:1 but less than 2:1, e.g. greater than 1:1 but less than 5:1, 10:1, 20:1, 30:1, 40:1, 50:1, 100:1, 200:1, 250:1, 500:1, 1000:1, 1500:1, 2000:1, 5000:1, 10000:1, 50000:1 or 100000:1.

Nevertheless, the foregoing should not be taken to exclude certain embodiments, e.g. those in which the difference between the CMC values for each non-ionic surfactant is sufficiently great, in which the mass concentration of surfactant$_{CMC\text{-}low}$ in the aqueous liquid composition may be lower than the mass concentration of surfactant$_{CMC\text{-}high}$. The skilled man would be able to determine if such an approach is viable and/or desirable by simply considering the respective CMC values of his chosen non-ionic surfactants. He would further be able to easily determine from the relevant CMC values the extent to which the mass concentration of surfactant$_{CMC\text{-}low}$ may be lower than the mass concentration of surfactant$_{CMC\text{-}high}$.

In these embodiments it is preferred that the mass concentrations of each non-ionic surfactant in the aqueous liquid composition will be selected such that the dilution achieves a concentration of surfactant$_{CMC\text{-}high}$ in the liquid preparation comprising crystalline particles of antimicrobial agent of step (ii) of 0.0001 to 1 times the CMC of the surfactant$_{CMC\text{-}high}$, e.g. 0.0005 to 1, 0.001 to 1, 0.005 to 1, 0.01 to 1, 0.05 to 1, 0.1 to 1, 0.5 to 1, preferably 0.0001 to 0.99 times the CMC of surfactant$_{CMC\text{-}high}$, e.g. 0.0005 to 0.99, 0.001 to 0.99, 0.005 to 0.99, 0.01 to 0.99, 0.05 to 0.99, 0.1 to 0.99, 0.5 to 0.99, 0.0005 to 0.95, 0.001 to 0.95, 0.005 to 0.95, 0.01 to 0.95, 0.05 to 0.95, 0.1 to 0.95, 0.5 to 0.95, 0.001 to 0.9, 0.005 to 0.9, 0.01 to 0.9, 0.05 to 0.9, 0.1 to 0.9, 0.5 to 0.9, 0.001 to 0.8, 0.005 to 0.8, 0.01 to 0.8, 0.05 to 0.8, 0.1 to 0.8, 0.5 to 0.8, 0.001 to 0.7, 0.005 to 0.7, 0.01 to 0.7, 0.05 to 0.7, 0.1 to 0.7, 0.5 to 0.7, 0.001 to 0.6, 0.005 to 0.6, 0.01 to 0.6, 0.05 to 0.6, 0.1 to 0.6, 0.5 to 0.6, 0.001 to 0.5, 0.005 to 0.5, 0.01 to 0.5, 0.05 to 0.5, 0.1 to 0.5, 0.15 to 0.2, 0.15 to 0.25, 0.15 to 0.30, 0.15 to 0.35, 0.15 to 0.4, 0.15 to 0.45, 0.15 to 0.5, 0.2 to 0.25, 0.2 to 0.30, 0.2 to 0.35, 0.2 to 0.4, 0.2 to 0.45, 0.2 to 0.5, 0.25 to 0.30, 0.25 to 0.35, 0.25 to 0.4, 0.25 to 0.45, 0.25 to 0.5, 0.30 to 0.35, 0.3 to 0.4, 0.3 to 0.45, 0.3 to 0.5, 0.35 to 0.4, 0.35 to 0.45, 0.35 to 0.5, 0.4 to 0.45, 0.4 to 0.5 or 0.45 to 0.5 times the CMC of surfactant$_{CMC\text{-}high}$.

In other embodiments the concentrations of each non-ionic surfactant will be selected such that the dilution achieves a concentration of surfactant$_{CMC\text{-}low}$ in the liquid preparation comprising crystalline particles of the antimicrobial agent of step (ii) of 0.0001 to 20 times the CMC of surfactant$_{CMC\text{-}low}$, e.g. 0.0005 to 20, 0.001 to 20, 0.005 to 20, 0.01 to 20, 0.05 to 20, 0.1 to 20, 0.5 to 20, 1 to 20, 5 to 20, 10 to 20, 15 to 20, 0.0005 to 15, 0.001 to 15, 0.005 to 15, 0.01 to 15, 0.05 to 15, 0.1 to 15, 0.5 to 15, 1 to 15, 5 to 15, 10 to 15, 0.01 to 10, 0.05 to 10, 0.1 to 10, 0.5 to 10, 1 to 10, 5 to 10, 0.01 to 5, 0.05 to 5, 0.1 to 5, 0.5 to 5, 0.01 to 1, 0.05 to 1, 0.1 to 1, 0.5 to 1, 0.01 to 0.5, 0.05 to 0.5, 0.1 to 0.5, 0.15 to 0.2, 0.15 to 0.25, 0.15 to 0.30, 0.15 to 0.35, 0.15 to 0.4, 0.15 to 0.45, 0.15 to 0.5, 0.2 to 0.25, 0.2 to 0.30, 0.2 to 0.35, 0.2 to 0.4, 0.2 to 0.45, 0.2 to 0.5, 0.25 to 0.30, 0.25 to 0.35, 0.25 to 0.4, 0.25 to 0.45, 0.25 to 0.5, 0.30 to 0.35, 0.3 to 0.4, 0.3 to 0.45, 0.3 to 0.5, 0.35 to 0.4, 0.35 to 0.45, 0.35 to 0.5, 0.4 to 0.45, 0.4 to 0.5 or 0.45 to 0.5 times the CMC of surfactant$_{CMC\text{-}low}$.

If the selected non-ionic surfactant (surfactant$_{belowCMC}$) is surfactant$_{CMC\text{-}low}$, surfactant$_{CMC\text{-}low}$ should preferably be present in the aqueous liquid composition at a mass concentration which is less than that of surfactant$_{CMC\text{-}high}$. In these embodiments, this may be expressed as a mass concentration ratio of surfactant$_{CMC\text{-}low}$ to surfactant$_{CMC\text{-}high}$ of less than 1:1, e.g. no more than 1:2, 1:5, 1:10, 1:20, 1:30, 1:40, 1:50, 1:100, 1:150, 1:200, 1:250, 1:500, 1:1000, 1:1500, 1:2000, 1:5000, 1:10000, 1:50000, or 1:100000. Expressed differently "less than" may be expressed as a mass concentration ratio of surfactant$_{CMC\text{-}low}$ to surfactant$_{CMC\text{-}high}$ of less than 1:1 but greater than 1:100000, e.g. less than 1:1 but greater than 1:50000, 1:10000, 1:5000, 1:2000, 1:1500, 1:1000, 1:500, 1:250, 1:200, 1:150, 1:100, 1:50, 1:40, 1:30, 1:20, 1:10, 1:5 or 1:2.

In this embodiment it is preferred that the concentrations of each non-ionic surfactant in the aqueous liquid composition will be selected such that dilution achieves a concentration of surfactant$_{CMC\text{-}low}$ in the liquid preparation comprising crystalline particles of antimicrobial agent of step (ii) of 0.0001 to 1 times the CMC of the surfactant$_{CMC\text{-}low}$, e.g. 0.0005 to 1, 0.001 to 1, 0.005 to 1, 0.01 to 1, 0.05 to 1, 0.1 to 1, 0.5 to 1, preferably 0.0001 to 0.99 times the CMC of surfactant$_{CMC\text{-}low}$, e.g. 0.0005 to 0.99, 0.001 to 0.99, 0.005 to 0.99, 0.01 to 0.99, 0.05 to 0.99, 0.1 to 0.99, 0.5 to 0.99, 0.0005 to 0.95, 0.001 to 0.95, 0.005 to 0.95, 0.01 to 0.95, 0.05 to 0.95, 0.1 to 0.95, 0.5 to 0.95, 0.001 to 0.9, 0.005 to 0.9, 0.01 to 0.9, 0.05 to 0.9, 0.1 to 0.9, 0.5 to 0.9, 0.001 to 0.8, 0.005 to 0.8, 0.01 to 0.8, 0.05 to 0.8, 0.1 to 0.8, 0.5 to 0.8, 0.001 to 0.7, 0.005 to 0.7, 0.01 to 0.7, 0.05 to 0.7, 0.1 to 0.7, 0.5 to 0.7, 0.001 to 0.6, 0.005 to 0.6, 0.01 to 0.6, 0.05 to 0.6, 0.1 to 0.6, 0.5 to 0.6, 0.001 to 0.5, 0.005 to 0.5, 0.01 to 0.5, 0.05 to 0.5, 0.1 to 0.5, 0.15 to 0.2, 0.15 to 0.25, 0.15 to 0.30, 0.15 to 0.35, 0.15 to 0.4, 0.15 to 0.45, 0.15 to 0.5, 0.2 to 0.25, 0.2 to 0.30, 0.2 to 0.35, 0.2 to 0.4, 0.2 to 0.45, 0.2 to 0.5, 0.25 to 0.30, 0.25 to 0.35, 0.25 to 0.4, 0.25 to 0.45, 0.25 to 0.5, 0.30 to 0.35, 0.3 to 0.4, 0.3 to 0.45, 0.3 to 0.5, 0.35 to 0.4, 0.35 to 0.45, 0.35 to 0.5, 0.4 to 0.45, 0.4 to 0.5 or 0.45 to 0.5 times the CMC of surfactant$_{CMC\text{-}low}$.

In these embodiments the concentrations of each non-ionic surfactant will be selected such that the dilution achieves a concentration of surfactant$_{CMC\text{-}high}$ in the liquid preparation comprising crystalline particles of the antimicrobial agent of step (ii) of 0.0001 to 20 times the CMC of surfactant$_{CMC\text{-}high}$ e.g. 0.0005 to 20, 0.001 to 20, 0.005 to 20, 0.01 to 20, 0.05 to 20, 0.1 to 20, 0.5 to 20, 1 to 20, 5 to 20, 10 to 20, 15 to 20, 0.0005 to 15, 0.001 to 15, 0.005 to 15, 0.01 to 15, 0.05 to 15, 0.1 to 15, 0.5 to 15, 1 to 15, 5 to 15, 10 to 15, 0.01 to 10, 0.05 to 10, 0.1 to 10, 0.5 to 10, 1 to 10, 5 to 10, 0.01 to 5, 0.05 to 5, 0.1 to 5, 0.5 to 5, 0.01 to 1, 0.05 to 1, 0.1 to 1, 0.5 to 1, 0.01 to 0.5, 0.05 to 0.5, 0.1 to 0.5, 0.15 to 0.2, 0.15 to 0.25, 0.15 to 0.30, 0.15 to 0.35, 0.15 to 0.4, 0.15 to 0.45, 0.15 to 0.5, 0.2 to 0.25, 0.2 to 0.30, 0.2 to 0.35, 0.2 to 0.4, 0.2 to 0.45, 0.2 to 0.5, 0.25 to 0.30, 0.25 to 0.35, 0.25 to 0.4, 0.25 to 0.45, 0.25 to 0.5, 0.30 to 0.35, 0.3 to 0.4, 0.3 to 0.45, 0.3 to 0.5, 0.35 to 0.4, 0.35 to 0.45, 0.35 to 0.5, 0.4 to 0.45, 0.4 to 0.5 or 0.45 to 0.5 times the CMC of surfactant$_{CMC\text{-}high}$.

In other embodiments of the multi-surfactant arrangements of the invention, dilution of each non-ionic surfactant is to a concentration at or below its CMC. In such embodiments the concentrations of each non-ionic surfactant in the aqueous liquid composition will be selected such that the dilution achieves concentrations of each non-ionic surfactant in the arrangement in the liquid preparation of step (ii), e.g. surfactant$_{CMC\text{-}high}$ and surfactant$_{CMC\text{-}low}$ in a two surfactant arrangement, independently being 0.0001 to 1 times the CMC of the respective surfactants, e.g. 0.0005 to 1, 0.001 to 1, 0.005 to 1, 0.01 to 1, 0.05 to 1, 0.1 to 1, 0.5 to 1, preferably 0.0001 to 0.99 times the CMC of the respective surfactants, e.g. 0.0005 to 0.99, 0.001 to 0.99, 0.005 to 0.99, 0.01 to 0.99, 0.05 to 0.99, 0.1 to 0.99, 0.5 to 0.99, 0.0005 to 0.95, 0.001 to 0.95, 0.005 to 0.95, 0.01 to 0.95, 0.05 to 0.95, 0.1 to 0.95, 0.5 to 0.95, 0.001 to 0.9, 0.005 to 0.9, 0.01 to 0.9, 0.05 to 0.9, 0.1 to 0.9, 0.5 to 0.9, 0.001 to 0.8, 0.005 to 0.8, 0.01 to 0.8, 0.05 to 0.8, 0.1 to 0.8, 0.5 to 0.8, 0.001 to 0.7, 0.005 to 0.7, 0.01 to 0.7, 0.05 to 0.7, 0.1 to 0.7, 0.5 to 0.7, 0.001 to 0.6, 0.005 to 0.6, 0.01 to 0.6, 0.05 to 0.6, 0.1 to 0.6, 0.5 to 0.6, 0.001 to 0.5, 0.005 to 0.5, 0.01 to 0.5, 0.05 to 0.5, 0.1 to 0.5, 0.15 to 0.2, 0.15 to 0.25, 0.15 to 0.30, 0.15 to 0.35, 0.15 to 0.4, 0.15 to 0.45, 0.15 to 0.5, 0.2 to 0.25, 0.2 to 0.30, 0.2 to 0.35, 0.2 to 0.4, 0.2 to 0.45, 0.2 to 0.5, 0.25 to 0.30, 0.25 to 0.35, 0.25 to 0.4, 0.25 to 0.45, 0.25 to 0.5, 0.30 to 0.35, 0.3 to 0.4, 0.3 to 0.45, 0.3 to 0.5, 0.35 to 0.4, 0.35 to 0.45, 0.35 to 0.5, 0.4 to 0.45, 0.4 to 0.5 or 0.45 to 0.5 times the CMCs of the respective non-ionic surfactants.

In certain embodiments of the multi-surfactant arrangements of the invention the non-ionic surfactants are selected to have differing CMCs, although in some embodiments the CMCs of each non-ionic surfactant will be the same or substantially the same. As mentioned above, for the purposes of comparison between CMC values, such values should be expressed as molar concentrations (i.e. as M, mM, μM, etc., as appropriate). Preferably in these multi-surfactant embodiments, the CMC of one non-ionic surfactant will be 1.1 to 20 times that of another non-ionic surfactant in the system, e.g. 1.1 to 15, 1.1 to 10, 1.1 to 9, 1.1 to 8, 1.1 to 7, 1.1 to 6, 1.1 to 5, 1.1 to 4, 1.1 to 3, 1.1 to 2, 1.5 to 20, 1.5 to 15, 1.5 to 10, 1.5 to 9, 1.5 to 8, 1.5 to 7, 1.5 to 6, 1.5 to 5, 1.5 to 4, 1.5 to 3, 1.5 to 2, 2 to 20, 2 to 15, 2 to 10, 2 to 9, 2 to 8, 2 to 7, 2 to 6, 2 to 5, 2 to 4, 2 to 3, 5 to 20, 5 to 15, 5 to 10, 5 to 9, 5 to 8, 5 to 7, 5 to 6, 6 to 20, 6 to 15, 6 to 10, 6 to 9, 6 to 8, 6 to 7, 10 to 20, 10 to 15, or 15 to 20 times that of another non-ionic surfactant in the system. As will be discussed in more detail below, the CMCs of the non-ionic surfactants of use in the present invention, including the above described multi-surfactant embodiments, may range from 0.1 to 50 mM. In preferred embodiments the CMC of surfactant$_{CMC\text{-}low}$ will range from 0.5 to 10 mM, e.g. from 0.75 to 5 mM, 1 to 4 mM or 1 to 3 mM.

Non-ionic surfactants and combinations of non-ionic surfactants suitable for use in the invention may readily be determined by those skilled in the art having in mind the criteria set out herein.

Non-ionic surfactants of use in the invention may be selected from polyoxyethylene glycol alkyl ethers ($CH_3$—$(CH_2)_{10\text{-}16}$—(O—$C_2H_4)_{1\text{-}25}$—OH, e.g. octaethylene glycol monododecyl ether and pentaethylene glycol monododecyl ether), polyoxypropylene glycol alkyl ethers ($CH_3$—$(CH_2)_{10\text{-}16}$—(O—$C_3H_6)_{1\text{-}25}$—OH), glycoside alkyl ethers (also known as alkyl (poly)glycosides: $CH_3$—$(CH_2)_{4\text{-}20}$-(glycone)$_{1\text{-}3}$-OH, e.g. decyl glucoside, lauryl glucoside, octyl glucoside, decyl maltopyranoside, octyl maltopyranoside, octyl thioglucopyranoside, n-heptyl thioglucopyranoside), acyl-N-methyl glucamides (e.g. MEGA 8, 9 (N-nonanoyl-N-methylglucamine) and 10), polyoxyethylene glycol octylphenol ethers ($C_8H_{17}$—($C_6H_4$)—(O—$C_2H_4)_{1\text{-}25}$—OH, e.g. Triton X-100), polyoxyethylene glycol alkylphenol ethers ($C_9H_{19}$—($C_6H_4$)—(O—$C_2H_4)_{1\text{-}25}$—OH, e.g. Nonoxynol-9), glycerol alkyl esters (e.g. glyceryl laurate), polyoxyethylene glycol sorbitan alkyl esters (e.g. polysorbate), sorbitan alkyl esters (e.g. Spans), cocamide MEA, cocamide DEA, dodecyldimethylamine oxide, block copolymers of polyethylene glycol and polypropylene glycol (e.g. poloxamers), polyethoxylated tallow amine (POEA). In certain embodiments the non-ionic surfactant is not an antimicrobial non-ionic surfactant.

Preferably the non-ionic surfactant or at least one of the non-ionic surfactants (where a mixture is used) is an alkyl (poly)glycoside represented by Formula I:

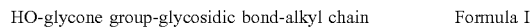

HO-glycone group-glycosidic bond-alkyl chain      Formula I

Preferably the glycone group is a monosaccharide, disaccharide or trisaccharide or sugar derivatives thereof such as aldonic and uronic acids, deoxy or amino sugars, sulfated sugars, and sugar alcohols. Where the glycone group is a monosaccharide the surfactant is strictly be referred to as an alkylglycoside. Where the glycone group consists of a plurality of monosaccharide units, the surfactant is strictly referred to as an alkylpolyglycoside.

The monosaccharide or one or more of the monosaccharide residues of the disaccharide or trisaccharide may be a triose, a tetrose, a pentose, a hexose, a heptose, an octose, a nonose or a decose in pyranose or furanose form and/or L- or D-form where appropriate and/or sugar derivatives thereof. Pentose or hexose saccharides/residues are preferred, e.g. mannose (e.g. D-mannose), galactose (e.g. D-galactose), glucose (e.g. D-glucose), fructose, fucose (e.g. L-fucose), N-acetyl-glucosamine, N-acetylgalactosamine, rhamnose, galactosamine, glucosamine (e.g. D-glucosamine), galacturonic acid, glucuronic acid, N-acetylneuraminic acid, methyl D-mannopyranoside (mannoside), a-methyl-glucoside, galactoside, ribose, xylose, arabinose, saccharate, mannitol, sorbitol, inositol, glycerol and derivatives of these monomers. The disaccharide may be exemplified by acarviosin, allolactose, cellobiose, chitobiose, galactose-alpha-1,3-galactose, dentiobiose, isomalt, isomaltose, isomaltulose, kojibiose, lactitol, lactobionic acid, lactose, lactulose, laminaribiose, maltitol, maltose, mannobiose, melibiose, melibiulose, neohesperidose, nigerose, robinose, rutinose, sambubiose, sophorose, sucralfate, sucralose, sucrose, sucrose acetate isobutyrate, sucrose octaacetate, trehalose, truranose, xylobiose or derivatives of these disaccharides.

The glycosidic bond may be an S-, N-, C-, or O-glycosidic bond.

Preferably the alkyl group contains 4 to 20 carbon atoms, e.g. 5 to 19, 6 to 18, 6 to 17, 6 to 16, 6 to 15, 6 to 14, 6 to 13, 6 to 12, 6 to 11, 6 to 10, 6 to 9, 6 to 8, 6 or 7, 7 to 16, 7 to 15, 7 to 14, 7 to 13, 7 to 12, 7 to 11, 7 to 10, 7 to 9, 7 or 8, 8 to 16, 8 to 15, 8 to 14, 8 to 13, 8 to 12, 8 to 11, 8 to 10, 8 or 9, 9 to 16, 9 to 15, 9 to 14, 9 to 13, 9 to 12, 9 to 11, 9 or 10, 10 to 16, 10 to 15, 10 to 14, 10 to 13, 10 to 12, 10 or 11, 11 to 16, 11 to 15, 11 to 14, 11 to 13, 11 or 12, 12 to 16, 12 to 15, 12 to 14, 12 or 13 carbon atoms, preferably 6, 7, 8, 9, 10 or 11 carbon atoms, more preferably 7, 8, 9 or 10 carbon atoms.

The alkyl group may be linear or branched, preferably linear. The alkyl group may be saturated, monounsaturated or polyunsaturated, preferably saturated.

The non-ionic surfactant preferably has a CMC of 0.1 mM to 50 mM, e.g. 0.5 mM to 45 mM, 0.5 mM to 40 mM, 0.5 mM to 30 mM, 0.5 mM to 25 mM, 0.5 mM to 20 mM, 0.75 mM to 45 mM, 0.75 mM to 40 mM, 0.75 mM to 30 mM, 0.75 mM to 25 mM, 0.75 mM to 20 mM, 1 mM to 45 mM, 1 mM to 40 mM, 1 mM to 30 mM, 1 mM to 25 mM, 1 mM to 20 mM, 1 mM to 15 mM, 1 mM to 10 mM, 1 mM to 5 mM, 1 mM to 3 mM, 1.5 mM to 45 mM, 1.5 mM to 40 mM, 1.5 mM to 30 mM, 1.5 mM to 25 mM, 1.5 mM to 20 mM, 2 mM to 45 mM, 2 mM to 40 mM, 2 mM to 30 mM, 2 mM to 25 mM or 2 mM to 20 mM.

Preferably the non-ionic surfactant is octyl- or decyl-glucoside, e.g. octyl β-D-glucopyranoside or decyl β-D-glucopyranoside or a mixture of octyl and/or decyl glucoside, e.g. a mixture having a mass percentage ratio (which may be calculated on volume by volume, or preferably a weight by weight, basis) of octyl to decyl of 1%:99%, 5%:95%, 10%:90%, 15%:85%, 20:80%, 25%:75%, 30%:70%, 35%:65%, 40%:60%, 55%:45%, 60%:40%, 65%:35%, 70%:30%, 75%:25%, 80%:20%, 85%:15%, 90%:10%, 95%:5% or 99%:1%. A mixture of 35-45% octyl and 65-55% decyl, e.g. 37-43% octyl and 63-57% decyl, 38-42% octyl and 62-58% decyl, 39-41% octyl and 61-59% decyl or about 40% octyl and about 60% decyl is an advantageous mixture in accordance with the invention. Such a mixture is available from commercial suppliers.

In certain embodiments the aqueous liquid composition will contain an antimicrobial agent, an octyl-glucoside and a decyl-glucoside and will be diluted to achieve the following concentrations of (i) antimicrobial (e.g. PPL), (ii) octyl- and (iii) decyl-glucoside: (i) antimicrobial: 1 ppm to 5000 ppm, e.g. 1 ppm to 2000 ppm, 1 ppm to 1000 ppm, 1 ppm to 500 ppm, 1 ppm to 400 ppm, 1 ppm to 300 ppm, 1 ppm to 200 ppm, 1 ppm to 100 ppm, 1 ppm to 50 ppm, 1 ppm to 25 ppm, 5 ppm to 2000 ppm, 5 ppm to 5000 ppm, 5 ppm to 2000 ppm, 5 ppm to 1000 ppm, 5 ppm to 500 ppm, 5 ppm to 400 ppm, 5 ppm to 300 ppm, 5 ppm to 200 ppm, 5 ppm to 100 ppm, 5 ppm to 50 ppm, 5 ppm to 25 ppm, 10 ppm to 5000 ppm, 10 ppm to 2000 ppm, 10 ppm to 1000 ppm, 10 ppm to 500 ppm, 10 ppm to 400 ppm, 10 ppm to 300 ppm, 10 ppm to 200 ppm, 10 ppm to 100 ppm, 10 ppm to 50 ppm, 10 ppm to 25 ppm, 20 ppm to 5000 ppm, 20 ppm to 2000 ppm, 20 ppm to 1000 ppm, 20 ppm to 500 ppm, 20 ppm to 400 ppm, 20 ppm to 300 ppm, 20 ppm to 200 ppm, 20 ppm to 100 ppm, 20 ppm to 50 ppm, 20 ppm to 25 ppm, 50 ppm to 5000 ppm, 50 ppm to 2000 ppm, 50 ppm to 1000 ppm, 50 ppm to 500 ppm, 50 ppm to 400 ppm, 50 ppm to 300 ppm, 50 ppm to 200 ppm, 50 ppm to 100 ppm, preferably 10 ppm to 200 ppm, 10 ppm to 150 ppm or 10 ppm to 100 ppm; (ii) octyl-glucoside: 10 ppm to 3000 ppm, e.g. 10 ppm to 2000 ppm, 10 ppm to 1000 ppm, 10 ppm to 500 ppm, 10 ppm to 400 ppm, 10 ppm to 300 ppm, 10 ppm to 200 ppm, 10 ppm to 100 ppm, 10 ppm to 50 ppm, 50 ppm to 3000 ppm, 50 ppm to 2000 ppm, 50 ppm to 1000 ppm, 50 ppm to 500 ppm, 50 ppm to 400 ppm, 50 ppm to 300 ppm, 50 ppm to 200 ppm, 50 ppm to 100 ppm, 100 ppm to 3000 ppm, 100 ppm to 2000 ppm, 100 ppm to 1000 ppm, 100 ppm to 500 ppm, 100 ppm to 400 ppm, 100 ppm to 300 ppm, 100 ppm to 200 ppm, 500 ppm to 3000 ppm, 500 ppm to 2000 ppm, 500 ppm to 1000 ppm, preferably 10 ppm to 1000 ppm, 10 ppm to 750 ppm, 10 ppm to 500 ppm or 10 ppm to 250 ppm; (iii) decyl-glucoside: 10 ppm to 3000 ppm, e.g. 10 ppm to 2000 ppm, 10 ppm to 1000 ppm, 10 ppm to 500 ppm, 10 ppm to 400 ppm, 10 ppm to 300 ppm, 10 ppm to 200 ppm, 10 ppm to 100 ppm, 10 ppm to 50 ppm, 50 ppm to 3000 ppm, 50 ppm to 2000 ppm, 50 ppm to 1000 ppm, 50 ppm to 500 ppm, 50 ppm to 400 ppm, 50 ppm to 300 ppm, 50 ppm to 200 ppm, 50 ppm to 100 ppm, 100 ppm to 3000 ppm, 100 ppm to 2000 ppm, 100 ppm to 1000 ppm, 100 ppm to 500 ppm, 100 ppm to 400 ppm, 100 ppm to 300 ppm, 100 ppm to 200 ppm, 500 ppm to 3000 ppm, 500 ppm to 2000 ppm, 500 ppm to 1000 ppm, preferably 10 ppm to 1000 ppm, 10 ppm to 750 ppm, 10 ppm to 500 ppm or 10 ppm to 250 ppm. The skilled man would appreciate that because the antimicrobial agent will be present to an extent in particulate form, the concentration ranges for the antimicrobial recited above are theoretical and are based on the concentration of the antimicrobial prior to dilution (the concentration in the aqueous liquid composition) and the dilution factor applied (the amount of aqueous solvent used in the dilution step).

In certain similar embodiments the aqueous liquid composition contain an antimicrobial agent and the abovementioned about 40/60 mix of octyl- and decyl-glucosides and will be diluted to achieve the following concentrations of (i) antimicrobial (e.g. PPL) and (ii) the abovementioned about 40/60 mix of octyl- and decyl-glucosides: (i) antimicrobial: 1 ppm to 5000 ppm, e.g. 1 ppm to 2000 ppm, 1 ppm to 1000 ppm, 1 ppm to 500 ppm, 1 ppm to 400 ppm, 1 ppm to 300 ppm, 1 ppm to 200 ppm, 1 ppm to 100 ppm, 1 ppm to 50 ppm, 1 ppm to 25 ppm, 5 ppm to 2000 ppm, 5 ppm to 5000 ppm, 5 ppm to 2000 ppm, 5 ppm to 1000 ppm, 5 ppm to 500 ppm, 5 ppm to 400 ppm, 5 ppm to 300 ppm, 5 ppm to 200 ppm, 5 ppm to 100 ppm, 5 ppm to 50 ppm, 5 ppm to 25 ppm, 10 ppm to 5000 ppm, 10 ppm to 2000 ppm, 10 ppm to 1000 ppm, 10 ppm to 500 ppm, 10 ppm to 400 ppm, 10 ppm to 300 ppm, 10 ppm to 200 ppm, 10 ppm to 100 ppm, 10 ppm to 50 ppm, 10 ppm to 25 ppm, 20 ppm to 5000 ppm, 20 ppm to 2000 ppm, 20 ppm to 1000 ppm, 20 ppm to 500 ppm, 20 ppm to 400 ppm, 20 ppm to 300 ppm, 20 ppm to 200 ppm, 20 ppm to 100 ppm, 20 ppm to 50 ppm, 20 ppm to 25 ppm, 50 ppm to 5000 ppm, 50 ppm to 2000 ppm, 50 ppm to 1000 ppm, 50 ppm to 500 ppm, 50 ppm to 400 ppm, 50 ppm to 300 ppm, 50 ppm to 200 ppm, 50 ppm to 100 ppm, preferably 10 ppm to 200 ppm, 10 ppm to 150 ppm or 10 ppm to 100 ppm; (ii) glucoside mix: 1 ppm to 5000 ppm, e.g. 1 ppm to 2000 ppm, 1 ppm to 1000 ppm, 1 ppm to 500 ppm, 1 ppm to 400 ppm, 1 ppm to 300 ppm, 1 ppm to 200 ppm, 1 ppm to 100 ppm, 1 ppm to 50 ppm, 1 ppm to 25 ppm, 5 ppm to 2000 ppm, 5 ppm to 5000 ppm, 5 ppm to 2000 ppm, 5 ppm to 1000 ppm, 5 ppm to 500 ppm, 5 ppm to 400 ppm, 5 ppm to 300 ppm, 5 ppm to 200 ppm, 5 ppm to 100 ppm, 5 ppm to 50 ppm, 5 ppm to 25 ppm, 10 ppm to 5000 ppm, 10 ppm to 2000 ppm, 10 ppm to 1000 ppm, 10 ppm to 500 ppm, 10 ppm to 400 ppm, 10 ppm to 300 ppm, 10 ppm to 200 ppm, 10 ppm to 100 ppm, 10 ppm to 50 ppm, 10 ppm to 25 ppm, 20 ppm to 5000 ppm, 20 ppm to 2000 ppm, 20 ppm to 1000 ppm, 20 ppm to 500 ppm, 20 ppm to 400 ppm, 20 ppm to 300 ppm, 20 ppm to 200 ppm, 20 ppm to 100 ppm, 20 ppm to 50 ppm, 20 ppm to 25 ppm, 50 ppm to 5000 ppm, 50 ppm to 2000 ppm, 50 ppm to 1000 ppm, 50 ppm to 500 ppm, 50 ppm to 400 ppm, 50 ppm to 300 ppm, 50 ppm to 200 ppm, 50 ppm to 100 ppm, preferably 10 ppm to 500 ppm, 10 ppm to 400 ppm, 10 ppm to 300 ppm or 10 ppm to 200 ppm.

In particularly preferred embodiments the aqueous liquid composition contains the antimicrobial agent at a concentration of 750 ppm to 1250 ppm, e.g. 800 ppm to 1200 ppm, 850 ppm to 1150 ppm, 900 ppm to 1100 ppm, 950 ppm to 1050 ppm, or about 1000 ppm, and the above mentioned 40/60 mix of octyl- and decyl-glucosides at a concentration of 750 ppm to 1250 ppm, e.g. 800 ppm to 1200 ppm, 850 ppm to 1150 ppm, 900 ppm to 1100 ppm, 950 ppm to 1050 ppm, e.g. about 1000 ppm.

The aqueous liquid composition may contain further surfactants, e.g. anionic, cationic or zwitterionic (amphoteric) surfactants. In certain embodiments these further surfactants may take the place of at least one of the two or more non-ionic surfactants in the above described embodiments. The particular features of the invention described as preferred or otherwise above should be applied mutatis mutandis to these embodiments. Preferably, in these embodiments, the further surfactant will take the place of the non-ionic surfactant which is not diluted to a concentration at or below its CMC.

The skilled man would appreciate that the charged nature of these surfactants may make them less or more compatible with the particular antimicrobial agent he is seeking to use in the methods of the invention. For instance, an anionic surfactant might not be wholly compatible with a negatively charged antimicrobial agent. Likewise a cationic surfactant might not be wholly compatible with a positively charged antimicrobial agent. Conversely an anionic surfactant might be especially compatible with a positively charged antimicrobial agent and a cationic surfactant might be especially compatible with a negatively charged antimicrobial agent. The skilled man would be able to take account of such issues from his common general knowledge. The skilled man would also appreciate that such charge implications could be mitigated or enhanced by incorporating further appropriately charged compounds into the surfactant-containing aqueous liquid composition of the method of the invention.

The anionic surfactant may be selected from sulfate, sulfonate, phosphate and carboxylate alkyl esters, preferably alkyl sulfates, alkyl phosphates and alkyl carboxylates. Alkyl sulfates may be exemplified by, but not limited to, ammonium lauryl sulfate, sodium lauryl sulfate (SDS; sodium dodecyl sulfate), sodium laureth sulfate (SLES; sodium lauryl ether sulfate) and sodium myreth sulfate. Alkyl carboxylates may be exemplified by, but not limited to, sodium stearate, sodium lauroyl sarcosinate, perfluorononanoate (PFNA) and perfluorooctanoate (PFOA).

The cationic surfactant may be selected from primary, secondary, or tertiary alkyl amines, e.g. octenidine dihydrochloride, and quaternary ammonium surfactants, which may be exemplified by, but not limited to, alkyltrimethylammonium salts (e.g. cetyl trimethylammonium bromide (CTAB, cetyl trimethylammonium chloride (CTAC)) benzalkonium chloride (BAC; also known as alkyl-dimethylbenzyl ammonium chloride), benzethonium chloride cetalkonium chloride, cetylpyridinium chloride, cetrimonium, didecyldimethylammonium chloride (DDQ), dioctadecyldimethylammonium bromide (DODAB) and domiphen bromide. Preferably the cationic surfactant is a quaternary ammonium surfactant, e.g. benzalkonium chloride (preferably benzyl-C12-16-alkyldimethyl chlorides) and didecyldimethylammonium chloride.

The zwitterionic surfactant may be selected from, for example, the alkyl betaines, the alkylamidopropylbetaines, the alkyl aminopropionates, the alkyliminodipropionates and the alkylimidazolines, e.g. lauryldimethylamine-N-oxide, n-dodecyl-N,N-dimethyl-3-ammonio-1-propanesulfonate, n-decyl-N,N-dimethylamine-N-oxide, n-decyl-N,N-dimethylglycine.

In certain embodiments the aqueous liquid composition does not contain anionic, zwitterionic and/or cationic surfactants that have a CMC greater than 30 mM. In certain embodiments the aqueous liquid composition does not contain anionic and/or zwitterionic surfactants. In other embodiments the aqueous liquid composition does not contain cationic surfactants that are not quaternary ammonium surfactants, e.g. benzalkonium chloride and didecyldimethylammonium chloride.

In preferred embodiments the only surfactants in detectable amounts in the aqueous liquid composition are non-ionic surfactants. In certain embodiments such non-ionic surfactants will not be antimicrobial. In other preferred embodiments the only surfactants in detectable amounts in the aqueous liquid composition are two different non-ionic surfactants, e.g. two different alkyl (poly)glycosides, e.g. octyl- and decyl-glucoside, e.g. octyl β-D-glucopyranoside and decyl β-D-glucopyranoside. In further preferred embodiments the only surfactant in detectable amounts in the aqueous liquid composition is a single non-ionic surfactant, e.g. octyl- or decyl-glucoside, e.g. octyl β-D-glucopyranoside or decyl β-D-glucopyranoside.

"Antimicrobial" in accordance with the invention means the ability of an agent to kill, destroy, or inhibit the growth of, microorganisms. This may therefore be a microbicidal activity and/or a microbiostatic activity.

More particularly, the term "microbicidal" means the ability negatively to impact the viability (i.e. to reduce or inhibit or ablate the viability) of a microorganism. In particular, "microbicidal" means the ability to kill or destroy a microorganism. The terms "kill" and "destroy" encompass the complete or partial destruction of the microorganism, e.g. the full or partial disintegration of the cellular structure of a microorganism. "Microbiostatic" means the ability to inhibit the growth of a microorganism. As described further below, the term "growth" is used broadly herein to refer to any aspect of growth of a microorganism, including both an increase in size or in the numbers of a microorganism. The term "growth" thus explicitly includes replication or reproduction of a microorganism. The term "inhibit" includes any degree of reduction of growth (as compared for example to growth which may be observed in the absence of the microbiostatic agent) as well prevention of growth.

The term "microbicidal" thus includes a cytotoxic effect of an agent against a microorganism. Therefore, a microbicidal agent can be viewed as bactericidal, fungicidal, algicidal, protozoacidal and so on depending on the type of microorganism that the agent is cytotoxic against. Similarly, the term "microbiostatic" can be viewed as a reference to a cytostatic effect of an agent against a microorganism. Therefore, in relation to the term "microbe" a microbiostatic agent can be categorised as bacteriostatic, fungistatic, algistatic, protozoastatic and so on depending on the type of microbe that the agent is cytostatic against.

The term "viability of a microorganism" means the ability of a microbe to survive under given conditions. Survival can be considered equivalent to remaining alive. Determining the viability of a microorganism can be done using the techniques detailed below for measuring microorganism cell death (and viability).

The term "killing a microorganism" refers to the act of causing a microorganism to cease to be alive, i.e. to become dead. A microorganism is considered to be alive if it can be induced to replicate and/or grow, or at least display morphological changes, when placed in a medium that would normally support the growth of that microorganism and/or the microorganism is metabolising nutrients to release energy to support cellular functions. Typically, a microorganism can be considered to be dead if cell membrane integrity is lost.

Many routine assays are available to determine if a microorganism is alive (viable) or dead. One option is to place the microorganism in conditions that would normally support the growth of that microorganism and monitor the growth of the microorganism by appropriate standard means, e.g. by monitoring the size of the microorganism, the morphology of the microorganism, the number of microorganisms in the colony over time, the consumption of nutrients in the culture media, etc. Another option is to assess the microorganism for morphologies characteristic of cell death, e.g. necrotic or apoptotic bodies, membrane blebs, nuclear condensation and cleavage of DNA into regularly sized fragments, ruptured cell walls or membranes and leakage of cell contents into the extracellular environment. Other methods exploit the characteristic loss of cell membrane integrity in dead microorganisms. Membrane impermeable dyes (e.g. trypan blue and propidium iodide) are routinely used to assess membrane integrity. A still further option is to measure the metabolism of the microorganism. This can be done routinely in a number of ways. For instance the levels of ATP can be measured By "growth of a microorganism" it is meant both an increase in the size of the microorganism or in the amount and/or volume of the constituents of a microorganism (e.g. the amount of nucleic acid, the amount of protein, the number of nuclei, the numbers or size of organelles, the volume of cytoplasm) and an increase in the numbers of a microorganism i.e. an increase in the replication of a microorganism.

By "inhibiting the growth of a microorganism" it is meant that measurable growth (e.g. replication) of a microorganism, or the rate thereof, is reduced. Preferably measurable growth (e.g. replication) of a microorganism, or the rate thereof, is reduced by at least 50%, more preferably at least 60%, 70%, 80% or 90%, e.g. at least 95%. Preferably, measurable growth (e.g. replication) is ceased. Growth in terms of microbial size increase or expansion etc. may be inhibited independently of replication and vice versa The antimicrobial agent which is the subject of the present invention is an antimicrobial peptide or an antimicrobial polyene, specifically a water soluble antimicrobial peptide or antimicrobial polyene having a molecular mass of 300 Da to 1 MDa and which is and capable of adopting at least one crystal form. The term Dalton may be used interchangeably with the term "unified atomic mass unit" (U). The unified atomic mass unit is defined as one twelfth of the mass of an atom of the nuclide 12C and has an approximate value of $1.6605655 \times 10^{-27}$ kg. 1 Da (Dalton or U) of a substance is also approximately equivalent to 1 g/mol. In certain embodiments the antimicrobial peptide is not an antibody or antibody fragment, e.g. a Fab fragment.

An antimicrobial peptide is a polymer of up to 100, e.g. up to 90, 80, 70, 60, 50, 40, 30 or 20 amino acids linked by peptide bonds that has antimicrobial activity under appropriate conditions, preferably not involving the action of an immune system. The polymer may be linear or cyclic, or partially linear and partially cyclic, and may also be branched. The peptide bonds of the peptide need not all involve the a carbon of the constituent amino acids, and may for instance involve the side chain amine group of lysine or another amino acid side chains containing amine groups, such as in ε-polylysine (PPL) produced by bacteria in the genus Streptomyces (e.g. Streptomyces albulus). Antimicrobial peptides typically have at least 5, e.g. at least 6, 7, 8, 9, 10, 11, 12, 13, 14, 15, 16, 17, 18 or 19 amino acids. Expressed differently an antimicrobial peptide may consist of about 5 to 100 amino acids, e.g. about 6 to 90, 7 to 80, 8 to 70, 9 to 60, 10 to 50, 11 to 50, 12 to 50, 13 to 40, 15 to 35, 20 to 40, 25 to 35 or 25 to 30 amino acids. PPL typically has 20 to 45, 20 to 40, 25 to 35 or 25 to 30 amino acids.

Antimicrobial peptides have been isolated from a diverse range of sources and display a diverse range of structures, but these structures have been well characterised and documented and as such the skilled man would readily be able to identify or recognise an antimicrobial peptide or determine if a novel peptide is an antimicrobial peptide from the literature, his common general knowledge and routine experimental techniques. The following databases are a selection of those available to the skilled man as a resource of information on antimicrobial peptides: CAMP, APD, DAMPD, YADAMP, PhytAMP, RAPD, Defensins knowledgebase, AMPer, DADP, BACTIBASE, Peptaibol Database PenBase Penaeidin, Database, AntiBP2, BAGEL2, and LAMP. Antimicrobial peptides may be divided into subgroups based on their amino acid composition and structure. Nearly all antimicrobial peptides are cationic and very often amphiphilic. They include one or more positively charged residues (arginine, lysine or, in acidic environments, histidine), and a large proportion (>50%) of hydrophobic residues. Antimicrobial peptides can be roughly categorized into those that have a high content of a certain amino acid, most often proline, but also lysine, glutamine and arginine, those that contain intramolecular disulfide bridges, and those with an amphiphilic region in their molecule if they assume an α-helical structure. Secondary structures of antimicrobial peptides can be α-helical, β-stranded due to the presence of 2 or more disulfide bonds, β-hairpin or loop due to the presence of a single disulfide bond and/or cyclisation of the peptide chain, and extended.

Included in the term antimicrobial peptide are the peptide antibiotics, e.g. actinomycin, bacitracin, colistin, and polymyxin B; the glycopeptide antibiotics, e.g. teicoplanin, vancomycin, telavancin; and the lantibiotics, e.g. nisin (the lantibiotic produced by *Lactococcus lactis*), bisin, subtilin, epidermin, gallidermin, mutacin, mersacidin, actagardine, duramycin, cinnamycin, haloduracin, sublancin and plantaricin C.

It is predicted that antimicrobial peptides that carry a net positive charge at or below physiological pH (e.g. about 7.2), like PPL, will crystallise well in the methods of the invention. As such, antimicrobial peptides having a net positive charge at or below physiological pH, e.g. a net charge of at least +1, e.g. at least +2, +3, +4, +5 or +10, are preferred. This may also be expressed as an average positive charge per amino acid in the peptide at or below physiological pH of 0.1 to 3, e.g. 0.2 to 2, 0.3 to 1, 0.4 to 1, 0.5 to 1, 0.6 to 1, 0.7 to 1, 0.8 to 1, 0.9 to 1, or 1 to 3.

Preferred antimicrobial peptides include peptides (e.g. as defined above) of 10 to 30 amino acids, e.g. 10 to 25, 10 to 20, 10 to 15, 15 to 30, 15 to 20, 15 to 25, 20 to 30, 20 to 25 and 25 to 30 amino acids having a net positive charge (e.g. as defined above) consisting of (i) lysine, arginine, glutamine and/or histidine and (ii) alanine, glycine, leucine, isoleucine, valine, methionine, proline, phenylalanine and/or tryptophan. In preferred embodiments option (i) is lysine and/or arginine, or more preferably, lysine. In other preferred embodiments option (ii) is alanine, glycine, leucine, isoleucine and/or valine, or, more preferably, alanine, glycine and/or leucine. In certain embodiments, option (i) is 1, 2, 3, 4, 5, 6, 7, 8, 9 or 10 lysine residues, e.g. 1 to 6 lysine residues, with the remainder of the peptide consisting of option (ii) as defined above, e.g. alanine, glycine and/or leucine.

In accordance with the invention ε-polylysine (PPL), nisin, polyarginine and polyglutamine are preferred antimicrobial peptides.

In accordance with the invention antimicrobial peptides that have activity against bacteria and/or fungi are preferred.

The antimicrobial agent may also be an antimicrobial polyene (e.g. a polyene antimycotic or polyene antibiotic), i.e. a polyene molecule that has antimicrobial activity, in particular antifungal/antimycotic activity, under appropriate conditions. Polyenes are poly-unsaturated organic compounds that contain one or more sequences of alternating double and single carbon-carbon bonds and would be immediate recognisable to the skilled man. Antimicrobial polyenes include, but are not limited to amphotericin B, nystatin, natamycin, rimocidin, filipin, hamycin, mepartricin and perimycin; amphotericin B, nystatin, natamycin being of note and natamycin most preferred.

By "water soluble" it is meant that the crystallisable antimicrobial agent can be dissolved to a concentration in the aqueous liquid composition adequate to permit crystallisation in accordance with the methods of the invention. Conveniently water soluble antimicrobial agents can be considered to be antimicrobial agents for which less than 1000 parts pure water are required to solubilise 1 part of the antimicrobial agent, e.g. less than 500, 250, 100, 50, 40, 30, 20, 10, 9, 8, 7, 6, 5, 4, 3, 2 or 1 parts pure water are required to solubilise 1 part of antimicrobial agent.

The crystallisable antimicrobial agent may have a molecular mass of 300 Da to 1 MDa. In certain embodiments the crystallisable antimicrobial agent has a molecular mass of any one of 300, 350, 400, 450, 500, 550, 600, 650, 700, 750, 800, 850, 900, 950, 1000, 1200, 1400, 1600, 1800, 2000, 2500, 3000, 3500, 4000, 4500, 5000, 6000, 7000, 8000, 9000, 10000, 150000, 20000, 30000 Da to any one of 40, 50, 100, 200, 300, 400, 500, 600, 700, 800, 900 kDa or 1 MDa. In other embodiments, antimicrobial agent molecule has a molecular mass of 300 Da to 200 kDa, e.g. 300 Da to 200, 150, 100, 50, 40, 30, 20, 15, 10, 9, 8, 7, 6, 5, 4, 3, 2 or 1 kDa, or 500 Da to 200, 150, 100, 50, 40, 30, 20, 15, 10, 9, 8, 7, 6, 5, 4, 3, 2 or 1 kDa, or 750 Da to 200, 150, 100, 50, 40, 30, 20, 15, 10, 9, 8, 7, 6, 5, 4, 3, 2 or 1 kDa, or 900 Da to 150, 100, 50, 40, 30, 20, 15, 10, 9, 8, 7, 6, 5, 4, 3, 2 or 1 kDa. In other embodiments, the crystallisable antimicrobial agent has a molecular mass of 1 kDa to 200 kDa, e.g. 1 kDa to 200, 150, 100, 50, 40, 30, 20, 15, 10, 9, 8, 7, 6, 5, 4, 3, or 2 kDa, or 2 kDa to 200, 150, 100, 50, 40, 30, 20, 15, 10, 9, 8, 7, 6, 5, 4 or 3 kDa, or 3 kDa to 200, 150, 100, 50, 40, 30, 20, 15, 10, 9, 8, 7, 6, 5 or 4 kDa.

The crystallisable antimicrobial agent to which the methods of the invention may be applied is a capable of adopting at least one crystal form under appropriate conditions, e.g. those of the conventional crystallisation techniques outlined above in the introduction. The skilled man would understand that not all water soluble antimicrobial peptides or polyenes of the appropriate size range are able to adopt a crystal form on account of their particular physical properties. For instance, particularly flexible polymers may not have the structural stability to form crystals. The skilled man would be able to identify likely crystallisation candidates from his common general knowledge. Nevertheless, without wishing to be bound by theory, it is believed that the present method is uniquely suited to the crystallisation of peptides or polyenes that may be considered difficult to crystallise on account of their flexibility because of the conformation that may be imposed by the micelles on the molecules during the execution of the method of the invention.

In certain embodiments more than one type of crystallisable antimicrobial agent (i.e. antimicrobial peptide or antimicrobial polyene) will be present in the aqueous liquid composition, e.g. at least 2, 3, 4, 5 or 10 different crystallisable antimicrobial agents will be present in the aqueous liquid composition and as a result the antimicrobial preparation of the invention will comprise crystalline particles containing a mixture of those crystallisable antimicrobial agents and/or a mixture of crystalline particles that substantially contain only one of the plurality of those different crystallisable antimicrobial agents. In these embodiments it may be advantageous to select crystallisable antimicrobial agents that have different target microorganisms, thereby expanding/tailoring the antimicrobial spectrum of the antimicrobial preparation. For instance, nisin is a broad-spectrum bacteriocin effective against many Gram-positive organisms (including *Clostridium botulinum*) and spores, PPL is effective against Gram-positive and Gram-negative organisms, fungi (including yeast) and viruses, and natamycin is highly effective against *Candida, Aspergillus, Cephalosporium, Fusarium* and *Penicillium*. Thus, by incorporating all three, or two of the three, a broader spectrum antimicrobial preparation may be obtained. In preferred embodiments of the method of the invention the aqueous liquid composition comprises (i) PPL, nisin or natamycin, (ii) PPL and nisin, (iii) PPL and natamycin, (iv) nisin and natamycin and (v) PPL, nisin and natamycin. In other embodiments of the method of the invention the aqueous liquid composition comprises at least one crystallisable antimicrobial peptide and at least one crystallisable polyene antibiotic, preferably together these agents have antimicrobial activity against gram-positive bacteria, gram negative bacteria and fungi (preferably including fungal spores) and preferably viruses.

The "aqueous liquid composition" is a composition in which the solvent portion is comprised substantially, e.g. predominantly or essentially of water, e.g. at least 80%, 90%, 95%, 99% or 100% of the solvent portion of the entity is water. In other embodiments less than 20%, 10%, 5%, or 1% of the solvent portion is a non-polar solvent, or at least the amount of non-polar solvent is insufficient to prevent the formation of crystalline particles of the antimicrobial agents in accordance with the invention, e.g. by interfering with micelle formation/disruption or the solubility of the surfactant and/or antimicrobial agent in the aqueous liquid composition. Solvents with a dielectric constant of less than 15 are generally considered to be non-polar. Expressed differently the aqueous liquid composition can be considered to comprise less than 20%, 10%, 5%, or 1% of a non-polar organic phase, or at least an amount of non-polar organic phase that is insufficient to prevent the formation of crystalline particles of the antimicrobial agents in accordance with the invention. Preferably the aqueous liquid composition is devoid of non-polar solvent/phase.

The presence of molecules or compounds other than the crystallisable antimicrobial agent (i.e. antimicrobial peptide or antimicrobial polyene) or the non-ionic surfactant, e.g. non-crystallisable and/or water insoluble molecules or compounds dissolved or suspended in the aqueous liquid composition is not excluded, so long as they are present in amounts that are insufficient to prevent the formation of crystalline particles of the antimicrobial agents in accordance with the invention. Organic molecules such as organic acids, alcohols, and sugars (e.g. saccharides, including glucose, sucrose, maltose, galactose, fructose) and food grade lipids may be incorporated. In certain embodiments the aqueous liquid composition does not contain an antimicrobial agent other than the antimicrobial peptides and/or antimicrobial polyenes for crystallisation. In other embodiments the only organic molecules in the aqueous liquid composition are the surfactants and the antimicrobial agents for crystallisation.

The aqueous liquid composition may also comprise molecules that ionise in the conditions of the aqueous liquid composition, e.g. salts, acids, alkalis and pH buffers. Preferably aqueous liquid composition has conductivity substantially within the parameters of drinking water.

In other embodiments the aqueous liquid composition contains only water, a crystallisable antimicrobial agent fraction (i.e. an antimicrobial peptide and/or an antimicrobial polyene, which may be a plurality of such agents) and a surfactant fraction (which may be a plurality of surfactants), e.g. a non-ionic surfactant fraction, to the substantial or essential exclusion of all other types of molecules.

The aqueous liquid composition may be prepared by any convenient means, e.g. by mixing solutions of each component or introducing each component individually or in combination to a single solution, or combination thereof. The order in which components are mixed or combined is also not important. However, in all instances, micelles of the at least one non-ionic surfactant and the organic molecule must be permitted to form prior to the dilution step(s). Typically, this will be instantaneous.

The "aqueous solvent" used to dilute the aqueous liquid composition may be a composition which is comprised substantially, e.g. predominantly or essentially of water, e.g. at least 80%, 90%, 95%, 99% or 100% of the solvent is water. In other embodiments less than 20%, 10%, 5%, or 1% of the solvent is a non-polar solvent, or at least the amount of non-polar solvent is insufficient to prevent the formation of crystalline particles of the antimicrobial agents in accordance with the invention, e.g. by interfering with micelle formation/disruption or the solubility of the surfactant and/or antimicrobial agent in the aqueous liquid composition. Expressed differently the aqueous solvent can be considered to comprise less than 20%, 10%, 5%, or 1% of a non-polar organic phase, or at least an amount of non-polar organic phase that is insufficient to prevent the formation of crystalline particles of the antimicrobial agents in accordance with the invention. Preferably the aqueous solvent is devoid of non-polar solvent/phase.

The presence of other molecules dissolved or suspended in the aqueous solvent is not excluded (e.g. those as described above), again as long as they are present in amounts that are insufficient to prevent the formation of crystalline particles of the antimicrobial agents in accordance with the invention. Preferably the aqueous solvent will not contain either or both of the crystallisable antimicrobial agent and non-ionic surfactant of the aqueous liquid composition. Preferably the aqueous solvent has conductivity substantially within the parameters of drinking water. Preferably the aqueous solvent may be substantially or essentially pure water.

Preferably dilution takes place in vitro. In a notable embodiment dilution takes place in the device from which the liquid preparation will be applied/administered to the treatment site, e.g. immediately prior to application or simultaneously with application. This device may be a spray device (e.g. as discussed below) in particular a misting system or infrastructure.

A typical misting system/infrastructure (which terms are used interchangeably) of use in accordance with the invention may comprise a spray nozzle (also referred to as an atomiser or a nebuliser) to which the liquid preparation of step (ii) (or the other antimicrobial liquid formulations of the invention discussed below) are delivered at sufficient pressure to atomise the liquid thereby producing a spray (mist) of suitable droplet size to effect successful administration/application to the treatment site and a remote reservoir of the liquid to be sprayed. Delivery of the liquid to the nozzle is typically via conduits (e.g. pipes, hosing, tubing or waterlines). In other embodiments a reservoir of the aqueous liquid composition of the invention is provided and dilution of that composition is effected in a separate reservoir or in the conduit between the reservoir of aqueous liquid composition and the spray nozzle. Thus, a preferred misting system of the invention may comprise a nozzle, a reservoir adapted to contain the aqueous liquid composition, a conduit between the reservoir and the nozzle and means for delivering the aqueous solvent of the invention to the aqueous liquid composition prior to its expulsion through the nozzle. The misting system may have a further reservoir adapted to contain the aqueous solvent. The misting system may be integrated within a building or structure or be free-standing.

The misting system may be manual, semi-automated or automated. The misting system may therefore be controlled by a computer program and thus a further component of a misting system of use in the invention may be a computer, system or apparatus carrying a program adapted to control the misting system, preferably adapted to perform an automated or semi-automated misting protocol.

Thus in a further aspect the invention provides a misting system, specifically a residual misting system (i.e. a system that provides a spray that leaves a residue on a treatment site) containing one or more spray nozzles, a first reservoir and a conduit between the first reservoir and the spray nozzles adapted to convey the contents of the first reservoir to the spray nozzle, wherein said first reservoir contains an antimicrobial preparation of the invention as defined herein. In preferred embodiments the misting system further comprises the means to deliver the aqueous solvent of the invention to the first reservoir, a mixing receptacle, the conduit or the nozzle thereby diluting at least a portion of the contents of the first reservoir. In further embodiments the misting system further comprises a second reservoir containing the aqueous solvent of the invention. In still further embodiments the misting system further comprises a computer, system or apparatus carrying a program adapted to control the misting system, preferably adapted to perform an automated or semi-automated misting protocol.

The method of preparing an antimicrobial preparation of the invention may further comprise a step of isolating at least a portion of said crystalline particles from said liquid preparation and/or removing at least a portion of the liquid phase of the liquid preparation to provide a more concentrated liquid preparation of crystalline particles. In these aspects of the invention the antimicrobial agent may further be an antimicrobial biguanide (e.g. polyaminopropyl biguanide (PAPB), polyhexamethylene biguanide (PHMB), chlorhexidine or alexidine).

By "isolation" it is meant that the crystalline particles of antimicrobial agent are separated from substantially, e.g. essentially, all of the components of the liquid preparation in which it has been formed, e.g. the liquid preparation of step (ii). Isolation may be performed in a single step or multiple steps. The multiple steps may be the same or different. An isolated crystalline particle of antimicrobial agent may be considered to be substantially, e.g. essentially free, of non-ionic surfactants, or any surfactant, and non-crystalline forms of the antimicrobial agent(s) of the crystalline particle. The skilled man would however understand that it might not be possible to render the crystalline particle of antimicrobial agent completely free of such entities.

Isolation of the crystalline particle of antimicrobial agent may be achieved by any convenient means. The skilled man would be aware of or be able to devise suitable procedures.

For instance the skilled man would be able to apply size filtration-based techniques by selecting filters or gels with appropriately sized pores, or chromatography columns with appropriately sized particulate solid supports, centrifugation-based techniques, gravity-based techniques (allowing the liquid preparation to stand for sufficient length of time for the crystalline particles to settle), and evaporation techniques. Washing steps with suitable buffers or water may be used before, after or between such techniques.

Concentration of the liquid preparation of step (ii) may be achieved by any convenient means that is able to reduce the volume of the liquid phase of the liquid preparation. This may be by techniques such as dialysis, filtration, evaporation, absorption and so on. The skilled man would be able to achieve such ends from his common general knowledge without undue burden.

In certain embodiments concentration and/or isolation does not involve a first substantial evaporation or drying stage. In other embodiments concentration and/or isolation does not involve any substantial evaporation or drying stage.

The concentrated liquid preparation of crystalline particles obtained from the method of the invention may be supplemented with further components, e.g those described above in connection with the supplementation of the liquid preparation obtained directly from the dilution step.

In another aspect the invention provides a liquid preparation obtained or obtainable from the method of the invention (as defined by steps (i) and (ii)) as described herein.

In a further aspect the invention provides an antimicrobial crystalline particle obtained or obtainable from the method of the invention described herein.

In a further aspect the invention provides a concentrated liquid preparation of crystalline particles of antimicrobial agent obtained or obtainable from the method of the invention (as defined by steps (i)-(iii)) as described herein).

The liquid preparation obtained from the method of the invention (i.e. that obtained from the culmination of steps (i) and (ii)) or the concentrated liquid preparation obtained from the method of the invention (i.e. that obtained from the culmination of steps (i) to (iii)) may be supplemented with further components, in particular further antimicrobial agents, but also, for instance, components to enhance storage life, sprayability and to meet safety requirements (e.g. dyes and bittering agents). The supplemental antimicrobial may be an antibiotic, an antiviral, an antifungal agent, a disinfectant, an antiseptic or a cleaning or sterilising agent. Antimicrobial surfactants are a class of supplemental antimicrobials of note. Examples of antimicrobial anionic surfactants include, but are not limited to, sodium dodecyl sulfate (sodium lauryl sulfate), sodium dodecyl aminopropionic acid, sodium ricinoleate, bile acids, alkylaryl sulfonates, Grillosan DS7911, disodium undecylenic acid monoethanol amidosulfosuccinate. Examples of antimicrobial cationic surfactants include, but are not limited to, the quaternary ammonium compounds, the aminimides and chlorhexidine compounds. Examples of antimicrobial non-ionic surfactants include, but are not limited to, the monoesters of fatty acids, polyethyleneglycomonoesters of alkyldihydroxybenzoic acids, glucosamine derivatives and diethanolamides of N-lauroyl dipeptides. Examples of antimicrobial amphoteric surfactants include, but are not limited to, the alkyl betaines, the alkylamidopropylbetaines, the alkyl aminopropionates, the alkyliminodipropionates and the alkylimidazolines.

In embodiments in which the antimicrobial crystalline particles comprise an antimicrobial peptide it may be advantageous to supplement the liquid preparation (or concentrated liquid preparation) with an antimicrobial polyene and/or an antimicrobial polybiguanide, e.g. in solution. Likewise, in embodiments in which the antimicrobial crystalline particles comprise an antimicrobial polyene, it may be advantageous to supplement the liquid preparation (or concentrated liquid preparation) with an antimicrobial peptide and/or an antimicrobial polybiguanide, e.g. in solution.

In other embodiments any supplemental antimicrobial agent is not an antimicrobial peptide or antimicrobial polyene or is not the same as the antimicrobial agent of the crystalline particles of the liquid preparations, i.e. is a further antimicrobial. In other embodiments the supplemental antimicrobial agent is not an antimicrobial surfactant.

Preferably the method of the invention comprises a further step of formulating the liquid preparation obtained from the method of the invention (i.e. that obtained from the culmination of steps (i) and (ii)), the concentrated liquid preparation obtained from the method of the invention (i.e. that obtained from the culmination of steps (i) to (iii)) or the crystalline particles obtained from the method of the invention (i.e. those obtained from the culmination of steps (i) to (iii)) with one or more excipients, e.g. excipients suitable for storage or for future use, e.g. in methods of combating contamination of a site with a microorganism, inhibiting the viability and/or growth of a microorganism in or on a subject, and combating, in particular in the treatment of, infection in or on an subject.

The crystalline particles or composition comprising same may be lyophilised.

The skilled man would know of suitable excipients for storage. Typical excipients in this context would be water, pH buffered water, oil, preservatives, antioxidants and stabilisers.

In a further aspect an antimicrobial liquid composition is provided comprising the following:
component A (ε-polylysine) at 4% to 0.001% w/w, preferably 2% to 0.01% w/w;
component B (octyl-glucoside) at 12% to 0.008% w/w, preferably 6% to 0.08% w/w;
component C (decyl-glucoside) at 16% to 0.012% w/w, preferably 8% to 0.12% w/w;
component D (benzalkonium chloride, e.g. benzyl-C12-16-alkyldimethyl chlorides) at 4% to 0.002% w/w, preferably 2% to 0.02% w/w; and component E (didecyldimethylammonium chloride) at 4% to 0.004% w/w, preferably 2% to 0.04% w/w.

Any ranges of percentage w/w which may be formed from the combination of respective upper and lower endpoints for each component are specifically contemplated.

The remaining percentage w/w (i.e. up to 100%) for the antimicrobial liquid composition will be provided by diluents, excipients, carriers or other active agents, although in preferred embodiments the antimicrobial liquid composition does not comprise further antimicrobial compounds or any further active agents (i.e. the only further compounds in the composition are inert, at least in the context of the combat of microorganisms as described herein). The antimicrobial liquid composition may therefore be described as comprising an antimicrobial fraction which fraction consists essentially of components A-E at the percentage weights recited herein and above.

In preferred embodiments the antimicrobial liquid composition is aqueous, e.g. at least 30% by weight, e.g. at least 35%, 40%, 45%, 50%, 55%, 60%, 65%, 70%, 75%, 80%, 85%, 90%, 95% or 99% of the antimicrobial liquid composition is an aqueous liquid, preferably water, allowance being made for the amounts of components A to E and any other excipients, carriers or other active agents which may be present.

In further preferred embodiments the antimicrobial liquid composition consists essentially of components A to E and water, i.e. any excipients, carriers or other active agents are present in negligible amounts. This may be expressed as an antimicrobial liquid composition consisting of the following:

component A at 4% to 0.001% w/w, preferably 2% to 0.01% w/w;
component B at 12% to 0.008% w/w, preferably 6% to 0.08% w/w;
component C at 16% to 0.012% w/w, preferably 8% to 0.12% w/w;
component D at 4% to 0.002%, preferably 2% to 0.02%;
component E at 4% to 0.004% w/w, preferably 2% to 0.04% w/w, less than about 5% w/w (e.g. less than about 4%, 3%, 2%, 1%, 0.5%, 0.1%, or 0.01% w/w) in total of excipients, carriers or active agents other than water, and
an amount of water sufficient to provide a total percentage w/w of 100%.

Any ranges of percentage w/w which may be formed from the combination of respective upper and lower endpoints for each component are specifically contemplated.

The selected percentage w/w of each component will be such that the liquid composition so formed will be antimicrobial as defined herein. In certain embodiments the selected percentage w/w of each component will be such that the liquid composition is antimicrobial following a 1:50 dilution, e.g. a 1:75, 1:100, 1:150, 1:200, 1:250, 1:300, 1:500 or 1:1000 dilution.

In one specific preferred embodiment the invention provides antimicrobial liquid composition consisting of the following:

ε-polylysine at about 2% w/w;
octyl-glucoside at about 6% w/w;
decyl-glucoside at about 8% w/w;
benzyl-C12-16-alkyldimethyl chlorides at about 2% w/w;
didecyldimethylammonium chloride at about 2% w/w, and
an amount of water sufficient to provide a total percentage w/w of 100%.

In a further specific preferred embodiment the invention provides antimicrobial liquid composition consisting of the following by weight percentage:

ε-polylysine at about 0.01% w/w;
octyl-glucoside at about 0.08% w/w;
decyl-glucoside at about 0.12% w/w;
benzyl-C12-16-alkyldimethyl chlorides at about 0.02% w/w;
didecyldimethylammonium chloride at about 0.04% w/w, and
an amount of water sufficient to provide a total percentage w/w of 100%.

It will also be seen from the foregoing that said components A to E may be present in the antimicrobial liquid composition in a ratio of 1:1.5:2:0.5:0.5 to 1:16:24:1:8, respectively, preferably 1:3:4:1:1 to 1:8:12:2:4, and any ratio ranges which may be formed from the combination of respective upper and lower endpoints for each component. In certain embodiments each number in the ratio may be prefaced by the term "about". The selected ratio will be such that the liquid composition so formed will be antimicrobial as defined herein.

In a further aspect the invention provides a method for combating contamination of a site with a microorganism, said method comprising contacting the site and/or the microorganism with an antimicrobial preparation of the invention (i.e. a liquid preparation of the invention, a concentrated liquid preparation of the invention, a crystalline particle of the invention, an antimicrobial liquid composition of the invention, or a composition comprising the same).

For the sake of brevity, in the following, references to an antimicrobial preparation of the invention are interchangeable with references to a liquid preparation of the invention, a concentrated liquid preparation of the invention, a crystalline particle of the invention an antimicrobial liquid composition of the invention, or a composition comprising the same.

More particularly the site (or location) and/or microorganism will be contacted with an effective amount of the antimicrobial preparation, more particularly an amount of the antimicrobial preparation sufficient to kill or inhibit the growth of the microorganism.

The site or location of the microorganism is not restricted. The microorganism may be present on a surface. The surface is not limited and includes any surface on which a microorganism may occur. The surface may be biotic or abiotic, and inanimate (or abiotic) surfaces include any such surface which may be exposed to microbial contact or contamination. Thus particularly included are large-scale industrial, agricultural and commercial surfaces, e.g. those on machinery, notably industrial machinery, or medical equipment or any surface exposed to an aquatic environment (e.g. marine equipment, or ships or boats or their parts or components), or any surface exposed to any part of the environment, e.g. pipes or on buildings. Such inanimate surfaces exposed to microbial contact or contamination include in particular any part of: food or drink processing, preparation, storage or dispensing machinery or equipment (in particular meat processing machinery or equipment and abattoir machinery or equipment, but also fruit and vegetable processing machinery or equipment), air conditioning apparatus, industrial machinery, e.g. in chemical or biotechnological processing plants, storage tanks, medical or surgical equipment and cell and tissue culture equipment. Any apparatus or equipment for carrying or transporting or delivering materials is susceptible to microbial contamination. Such surfaces will include particularly pipes (which term is used broadly herein to include any conduit or line). Representative inanimate or abiotic surfaces include, but are not limited to food processing, storage, dispensing or preparation equipment or surfaces, tanks, conveyors, floors, drains, coolers, freezers, equipment surfaces, walls, valves, belts, pipes, air conditioning conduits, cooling apparatus, food or drink dispensing lines, heat exchangers, boat hulls or any part of a boat's structure that is exposed to water, dental waterlines, oil drilling conduits, contact lenses and storage cases.

As noted above, medical or surgical equipment or devices represent a particular class of surface on which microbial contamination may form. This may include any kind of line, including catheters (e.g. central venous and urinary catheters), prosthetic devices e.g., heart valves, artificial joints, false teeth, dental crowns, dental caps and soft tissue implants (e.g. breast, buttock and lip implants). Any kind of implantable (or "in-dwelling") medical device is included (e.g. stents, intrauterine devices, pacemakers, intubation tubes (e.g. endotracheal or tracheostomy tubes), prostheses or prosthetic devices, lines or catheters). An "in-dwelling"

medical device may include a device in which any part of it is contained within the body, i.e. the device may be wholly or partly in-dwelling.

The surface can be made of any material. For example it may be metal, e.g. aluminium, steel, stainless steel, chrome, titanium, iron, alloys thereof, and the like. The surface can also be plastic, for example, polyolefin (e.g., polyethylene, (Ultra-High Molecular Weight) polyethylene, polypropylene, polystyrene, poly(meth)acrylate, acrylonitrile, butadiene, ABS, acrylonitrile butadiene, etc.), polyester (e.g., polyethylene terephthalate, etc.), and polyamide (e.g., nylon), combinations thereof, and the like. Other examples include acetal copolymer, polyphenylsulfone, polysulfone, polythermide, polycarbonate, polyetheretherketone, polyvinylidene fluoride, poly(methyl methacrylate) and poly(tetrafluoroethylene). The surface can also be silicon, brick, tile, ceramic, porcelain, wood, vinyl, linoleum, or carpet, combinations thereof, and the like. The surfaces can also be food, for example, beef, poultry, pork, vegetables, fruits, fish, shellfish, combinations thereof, and the like. Foodstuffs, such as those described above, in isolation from an animal or plant body, are considered inanimate for the purposes of the invention.

A biotic or animate surface may include any surface or interface in or on an animal, plant or fungal body. It may accordingly be viewed as a "physiological" or "biological" surface. It may be any internal or external body surface, including of any tissue or organ, which, in the case of an animal body, may include haematological or haematopoietic tissue (e.g. blood). Dead or dying (e.g. necrotic) or damaged (e.g. inflamed or disrupted or broken) tissue is particularly susceptible to microbiological contamination, and such tissue is encompassed by the term "animate" or "biotic". The surface may be a mucosal or non-mucosal surface.

Representative biotic surfaces include, but are not limited to, any surface in the oral cavity (e.g. teeth, gingiva, gingival crevice, periodontal pocket) the reproductive tract (e.g. cervix, uterus, fallopian tubes), the peritoneum, middle ear, prostate, urinary tract, vascular intima, eye, i.e. ocular tissue (e.g. the conjunctiva lachrymal duct, lachrymal gland, eyelid), corneal tissue, the respiratory tract, lung tissue (e.g. bronchial and alveolar), heart valves, gastrointestinal tract, skin, scalp, nails and the interior of wounds, particularly chronic wounds and surgical wounds, which may be topical or internal wounds. Other surfaces include the exterior of organs, particularly those undergoing transplantation, for example, heart, lungs, kidney, liver, heart valve, pancreas, intestine, corneal tissue, arterial and venous grafts and skin. Skin, wounds and transplant tissue are of note.

The location may also be a location that is not a surface. In other words the microorganism can be found within a material as well as on its surface. The material can be chemically heterogeneous as well as chemically homogenous. The material can also be constructed or formed from or comprise different parts or components. The material can be a part of a larger material or entity. The material may be or comprise the materials from which the above mentioned surfaces are formed. In some instances the material can be considered to be an object, which terms covers volumes of liquids wherever found. The material may comprise any of the above described surfaces.

The material may be abiotic or biotic (inanimate or animate) as is discussed above in relation to surfaces. For instance, the material might be, completely or in part, a solid, a liquid, a semi solid, a gel or a gel-sol. Thus, for example, the microorganism might be present in body fluids (e.g. blood, plasma, serum, cerebrospinal fluid, GI tract contents, semen); tissues (e.g. adrenal, hepatic, renal, pancreatic, pituitary, thyroid, immune, ovarian, testicular, prostate, endometrial, ocular, mammary, adipose, epithelial, endothelial, neural, muscle, pulmonary, epidermis, osseous); cell and tissue culture media; cell and tissue cultures; clinical/scientific waste materials (which can comprise any of the preceding materials); pharmaceuticals (e.g. tablets, pills, powders, lozenges, sachets, cachets, elixirs, suspensions, emulsions, solutions, syrups, aerosols, sprays, compositions for use in nebulisers, ointments, soft and hard gelatine capsules, suppositories, sterile injectable solutions, sterile packaged powders); animal or human food stuffs (e.g. meat, fish, shellfish, fruit, vegetables, cereals, dairy products, fruit juices, vegetable juices, sauces, stocks, soups, confectionary, alcoholic beverages, condiments); personal hygiene products (e.g. toothpaste, mouthwash, shampoo, soap, deodorant, shower gel); cosmetics (e.g. lip gloss, eye shadow, foundation); soil; drinking water supplies; waste water supplies; agricultural feedstuffs and water supplies; insecticide, pesticide and herbicide formulations; industrial lubricants and so on. Liquids, semi solids, gels or gel-sols are of note. The body fluids and tissues may be treated in vitro/ex vivo as well as it being possible to treat the same in vivo.

As will be clear from the foregoing, the site or location of the contamination or potential contamination is not restricted, e.g. it can be in vitro or in vivo, but particularly in this aspect of the invention it will be an "in vitro" or "ex vivo" site or location (i.e. an inanimate or abiotic site or location, or an animate or biotic site or location that is isolated from (not in or on) a human, animal, plant or fungal body). However, the site or location may be in or on a human or animal subject and in which case a therapeutically effective amount of the antimicrobial preparation is administered to the subject.

Thus, it can be seen that in one particular aspect the invention provides a method for inhibiting the viability and/or growth of a microorganism in or on a subject, said method comprising administering an effective amount of the antimicrobial preparation of the invention to a subject in need thereof.

Also provided is an antimicrobial preparation of the invention for use in inhibiting the viability and/or growth of a microorganism in or on a subject.

Alternatively put, this aspect of the invention provides the use of an antimicrobial preparation of the invention, for the manufacture of a medicament for inhibiting the viability and/or growth of a microorganism in or on a subject.

Viewed differently the invention provides an antimicrobial preparation of the invention for use as a therapeutic microbicidal and/or a microbiostatic agent and the use of an antimicrobial preparation of the invention, for the manufacture of a microbicidal and/or a microbiostatic medicament.

These aspects of the invention can also be seen to provide (i) a method for combating, and in particular in the treatment of, microbial infection in or on an subject said method comprising administering an effective amount of the antimicrobial preparation of the invention to a subject in need thereof; (ii) an antimicrobial preparation of the invention for use in combating, and in particular in the treatment of, microbial infection in or on an subject; or (iii) the use of an antimicrobial preparation of the invention, in the manufacture of a medicament for use in combating, and in particular in the treatment of, microbial infection in or on a subject. It will be seen in this aspect that the infection may be combated by inhibiting the growth and/or viability of a microorganism in or on a subject.

As indicated above, the above references to an antimicrobial preparation of the invention are interchangeable with references to a liquid preparation of the invention, a concentrated liquid preparation of the invention, a crystalline particle of the invention, an antimicrobial liquid composition of the invention, or a composition comprising the same.

Where a future use is in the combat of microbial contamination on an inanimate surface or in an inanimate material, i.e. not on or in a living human or animal body, the antimicrobial preparation of the invention, (i.e. the crystalline particles, liquid preparation, an antimicrobial liquid composition or concentrated liquid preparation of the invention where appropriate) may be applied to the surface or material to be treated in any convenient composition or formulation, or by any convenient means. For instance a liquid form of the antimicrobial preparation (in particular the liquid preparation of step (ii)) may simply be spayed onto the inanimate surface to be treated, e.g. via a misting system (as discussed above) or via a spray gun or other atomising device which may be manual, semi-automated or fully automated. Spraying may involve a propellant but preferably will be propellant free. Spray applications may involve a pre- and/or post application spraying of water or other aqueous solution. In other examples a liquid form of the antimicrobial preparation (in particular the liquid preparation of step (ii)) may be applied via a fabric or sponge wipe carrying the liquid antimicrobial preparation.

Thus the crystalline particles may be in liquid, gel, gel-sol, semi-solid or solid form (e.g. solutions, suspensions, homogenates, emulsions, pastes, powders, aerosols, vapours). Typically the compositions for treating such inanimate surfaces or materials will be a non-pharmaceutically acceptable composition. The choice of composition form will be dictated by the identity of the crystalline particles, the microbe on the surface or in the material and location of the surface or material. For instance, if the location is a fluid line it might be convenient to apply a fluid composition. It might also be preferred to use a composition that persists on the surface or in the part of the fluid line to be treated but that will not leach into the fluid of normal use, e.g. an adhesive gel. The skilled person is readily able to prepare suitable compositions from his common general knowledge. For instance, the antimicrobial preparation may be added to a paint formulation and applied to the surface to be treated, e.g. a boat hull or other part of a boat's structure that is exposed to water, or to a building or any part thereof, a tank (e.g. a storage or processing tank) or indeed to any part of any industrial machinery. Such compositions may conveniently also comprise a further anti-microbial agent, as described above, e.g. an antibiotic, chlorine bleach, TCP, ethanol, Virkon™, povidone-iodine, silver compounds, antimicrobial surfactants, etc., e.g. those discussed above. A combination of PPL-containing or PHMB-containing crystalline particles of the invention and non-crystalline nisin and/or natamycin in an aqueous solution is of particular note. As the compositions need not be pharmaceutically acceptable, harsher antimicrobials can be used subject to considerations of surface damage, environmental contamination, user safety and contamination of the treated surface and interaction with the other components of the composition.

Where a future use is in the combat of contamination on an animate surface on in an animate material, i.e. on or in a living human or animal body (in vivo), in other words as a pharmaceutical, the antimicrobial preparation may be applied to the surface or material to be treated in any convenient pharmaceutically acceptable composition or formulation. Such formulations can also be used in ex vivo treatments.

Thus, in a further embodiment there is provided a pharmaceutical composition comprising an antimicrobial preparation (i.e. a crystalline particle, liquid preparation or concentrated liquid preparation) of the invention as defined herein together with at least one pharmaceutically acceptable carrier, diluent or excipient.

The antimicrobial preparation may be incorporated, optionally together with other active agents, with one or more conventional carriers, diluents and/or excipients, to produce conventional galenic preparations such as tablets, pills, powders (e.g. inhalable powders), lozenges, sachets, cachets, elixirs, suspensions, emulsions, solutions, syrups, aerosols (as a solid or in a liquid medium), sprays (e.g. nasal sprays), compositions for use in nebulisers, ointments, soft and hard gelatine capsules, suppositories, sterile injectable liquid formulations, sterile packaged powders, and the like. Sterile inhalable compositions are of particular note for use in the treatment of respiratory diseases associated with microorganisms (which may include COPD, COAD, COAP, pneumonia, cystic fibrosis, emphysema and asthma).

Examples of suitable carriers, excipients, and diluents are lactose, dextrose, sucrose, sorbitol, mannitol, starches, gum acacia, calcium phosphate, inert alginates, tragacanth, gelatine, calcium silicate, microcrystalline cellulose, polyvinylpyrrolidone, cellulose, water syrup, water, water/ethanol, water/glycol, water/polyethylene, hypertonic salt water, glycol, propylene glycol, methyl cellulose, methylhydroxybenzoates, propyl hydroxybenzoates, talc, magnesium stearate, mineral oil or fatty substances such as hard fat or suitable mixtures thereof. Excipients and diluents of note are mannitol and hypertonic salt water (saline).

The compositions may additionally include lubricating agents, wetting agents, emulsifying agents, suspending agents, preserving agents, sweetening agents, flavouring agents, and the like.

Parenterally administrable forms, e.g., intravenous solutions or suspensions, should be sterile and free from physiologically unacceptable agents, and should have low osmolarity to minimize irritation or other adverse effects upon administration and thus such formulations should preferably be isotonic or slightly hypertonic, e.g. hypertonic salt water (saline). Suitable vehicles include aqueous vehicles customarily used for administering parenteral formulations such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975). The solutions can contain preservatives, further antimicrobial agents, buffers and antioxidants conventionally used for parenteral solutions, excipients and other additives which are compatible with the crystalline particles and which will not interfere with the manufacture, storage or use of products.

For topical administration the antimicrobial preparation can be incorporated into creams, ointments, gels, transdermal patches and the like or applied in a liquid formulation, e.g. an aqueous liquid formulation. This might involve application via a fabric or sponge wipe carrying the liquid formulation or by spraying the liquid formulation onto the treatment area, e.g. via the spray devices and misting systems described herein. The antimicrobial preparation of the invention can also be incorporated into medical dressings, for example wound dressings e.g. woven (e.g. fabric) dressings or non-woven dressings (e.g. gels or dressings with a gel component). Further topical systems that are envisaged to be suitable are in situ drug delivery systems, for example gels where solid, semi-solid, amorphous or liquid crystalline gel matrices are formed in situ and which may comprise the crystalline particles. For application to oral, buccal and dental surfaces, toothpastes, dental gels, dental foams, oral sprays and mouthwashes are mentioned specifically.

Inhalable compositions are also of note. The formulation of compositions suitable for inhalation is routine for the skilled man and has long been standard practice in the treatment of respiratory diseases. Inhalable compositions may, for instance, take the form of inhalable powders, solutions or suspensions. The skilled man would be able to select the most appropriate type of delivery system for his needs and be able to prepare a suitable formulation of the antimicrobial preparation of the invention for use in that system. Propellant-free nebulisable solutions and inhalable powder formulations are particularly preferred.

The subject may be any human or non-human animal subject, but more particularly may be a vertebrate, e.g. an animal selected from mammals, birds, amphibians, fish and reptiles. The animal may be a livestock or a domestic animal or an animal of commercial value, including laboratory animals or an animal in a zoo or game park. Representative animals therefore include dogs, cats, rabbits, mice, guinea pigs, hamsters, horses, pigs, sheep, goats, cows, chickens, turkeys, guinea fowl, ducks, geese, parrots, budgerigars, pigeons, salmon, trout, cod, haddock, sea bass and carp. Veterinary uses of the invention are thus covered. The subject may be viewed as a patient. Preferably the subject is a human.

The term "in a subject" is used broadly herein to include sites or locations inside a subject or on a subject, e.g. an external body surface, and may include in particular infection of a medical device e.g. an implanted or "in-dwelling" medical device.

"Combating contamination" includes both preventative and reactionary measures or treatments and therefore covers the prevention as well as the reduction, limitation, inhibition or elimination of contamination.

By "contamination" it is meant the unwanted presence of a microorganism at a particular site or location. In abiotic locations this can be considered at its extreme to refer to the presence of any microorganism at the site. Contamination can be considered to cover colonisation of a location by the microorganism, i.e. the establishment of a microorganism at a location and the expansion of the numbers of that microorganism by replication or the recruitment of additional microorganisms, which may be of the same or of a different type.

"Treatment" when used in relation to the treatment of a medical condition/infection in a subject in accordance with the invention is used broadly herein to include any therapeutic effect, i.e. any beneficial effect on the condition or in relation to the infection. Thus, not only included is eradication or elimination of the infection, or cure of the subject or infection, but also an improvement in the infection or condition of the subject. Thus included for example, is an improvement in any symptom or sign of the infection or condition, or in any clinically accepted indicator of the infection/condition (for example a decrease in wound size or an acceleration of healing time). Treatment thus includes both curative and palliative therapy, e.g. of a pre-existing or diagnosed infection/condition, i.e. a reactionary treatment.

"Prevention" as used herein refers to any prophylactic or preventative effect. It thus includes delaying, limiting, reducing or preventing the condition (which reference includes infection and contamination, as applicable, in the different aspects of the invention) or the onset of the condition, or one or more symptoms or indications thereof, for example relative to the condition or symptom or indication prior to the prophylactic treatment. Prophylaxis thus explicitly includes both absolute prevention of occurrence or development of the condition, or symptom or indication thereof, and any delay in the onset or development of the condition or symptom or indication, or reduction or limitation on the development or progression of the condition or symptom or indication.

The term "microorganism" as used herein includes any microbial organism, that is any organism that is microscopic, namely too small to be seen by the naked eye. In particular as used herein the term includes the organisms typically thought of as microorganisms, particularly bacteria, fungi, archaea, algae and protists. The term thus particularly includes organisms that are typically unicellular, but which may have the capability of organising into simple cooperative colonies or structures such as filaments, hyphae or mycelia (but not true tissues) under certain conditions. The microorganism may be prokaryotic or eukaryotic, and may be from any class, genus or species of microorganism. Examples of prokaryotic microorganisms include, but are not limited to, bacteria, including the mycoplasmas, (e.g. Gram-positive, Gram-negative bacteria or Gram test non-responsive bacteria) and archaeobacteria. Eukaryotic microorganisms include fungi, algae and others that are, or have been, classified in the taxonomic kingdom Protista or regarded as protists, and include, but are not limited to, for example, protozoa, diatoms, protoophyta, and fungus-like molds. The microorganism may be aerobic or anaerobic. The microorganism may be pathogenic or non-pathogenic, or a be spoilage or an indicator microorganism. In particular preferred embodiments the microorganism is pathogenic.

Bacteria or fungi represent preferred classes of microorganism.

The bacteria may be Gram positive or Gram negative bacteria, or indeed Gram-indeterminate bacteria. Preferably the bacteria are selected from the following genera: *Achromobacter, Acinetobacter, Actinobacillus, Aeromonas, Agrobacterium, Alcaligenes, Alteromonas, Bacteroides, Bartonella, Borrelia, Bordetella, Brucella, Burkholderia, Campylobacter, Cardiobacterium, Chlamydia, Chlamydophila, Chromobacterium, Chyseobacterium, Chryseomonas, Citrobacter, Clostridium, Comamonas, Corynebacterium, Coxiella, Cryptobacterium, Edwardsiella, Eikenella, Enterobacter, Enterococcus, Erwinia, Kingella, Klebsiella, Lactobacillus, Lactococcus, Legionella, Leptospira, Leptotrichia, Leuconostoc, Listeria, Listonella, Mobiluncus, Moraxella, Morganella, Mycobacterium, Mycoplasma, Neisseria, Nocardia, Nocardiopsis, Pantoea, Parachlamydia, Pasteurella, Peptococcus, Peptostreptococcus, Prevotella, Propionibacterium, Proteus, Providencia, Pseudomonas, Ralstonia, Rickettsia, Salmonella, Shewenella, Shigella, Sphingobacterium, Sphingomonas, Staphylococcus, Stenotrophomonas, Streptobacillus, Streptococcus, Streptomyces, Treponem* and *Yersinia.*

The microorganism may also be a, or from a, fungus, including for example fungi that may be, or may have been, classified as protista, e.g. fungi from the genera *Candida, Aspergillus, Pneumocystis, Penicillium* and *Fusarium.* Representative fungal species include, but are not limited to, *Candida albicans, Candida dubliniensis, Cryptococcus neo-* formans, Histoplama capsulatum, Aspergillus fumigatus, Coccidiodes immitis, Paracoccidioides brasiliensis, Blastomyces dermitidis, Pneomocystis carnii, Penicillium marneffi, Alternaria alternate.

The microorganism may also be an, or from an, alga, including for example algae that may be, or may have been, classified as protista. Representative algal species include *Chaetophora, Chlorella protothecoides, Coleochaete scutata, Coleochaete soluta, Cyanidioschyzon merolae Aphanochaete, Gloeotaenium, Oedogonium, Oocystis, Oscillatoria, Paradoxia multisitia, Phormidium, Chroococcus, Aphanothece, Fragillaria, Cocconis, Navicula, Cymbella, Phaeodactylum* as well as cyanobacteria (blue-green algae) and diatoms such as *Nitzschia palea*.

In one embodiment of this aspect the microorganism is in a biofilm.

In a further aspect the invention provides products susceptible to microbial contamination/colonisation whose susceptible surfaces have been pretreated with the crystalline particles of the invention as defined herein.

By "pretreated" it is meant that the susceptible surface is exposed to a crystalline particle of the invention prior to an exposure to microorganism and that the crystalline particle persists on the surface for a duration sufficient to prevent contamination/colonisation by a microorganism for an appreciable duration of time. Preferably the crystalline particle will persist for substantially the useful life of the surface, e.g. the pretreatment results in a substantially permanent coating of an crystalline particle. Thus a pre-treated surface/product is one to which the crystalline particle is applied and on which it remains. Such a product/surface may be a coated product/surface.

Non-limiting examples of products and surfaces susceptible to microbial contamination/colonisation are described above. Particular mention may be made of medical and surgical devices, food or drink processing, storage or dispensing equipment, in particular such equipment in meat processing plants and abattoirs, and food and drink stuffs, in particular meats, vegetables and fruits and processed products containing the same.

Pretreatment can be achieved by any convenient means, for example any form of applying the crystalline particle to the surface, notably coating (e.g. spray coating) the surface, e.g. with a liquid preparation or concentrated liquid preparation of the invention. Alternatively, the crystalline particle can be incorporated into the material from which the object or its susceptible parts are manufactured. This approach is suited to objects, or constituent parts thereof, manufactured from polymers such as plastics and silicones, e.g. the medical and surgical devices described above any the equipment of food processing plants.

The invention will be further described with reference to the following non-limiting Examples in which.

EXAMPLE 1—MATERIALS AND STANDARD METHODS

Figure 1A:
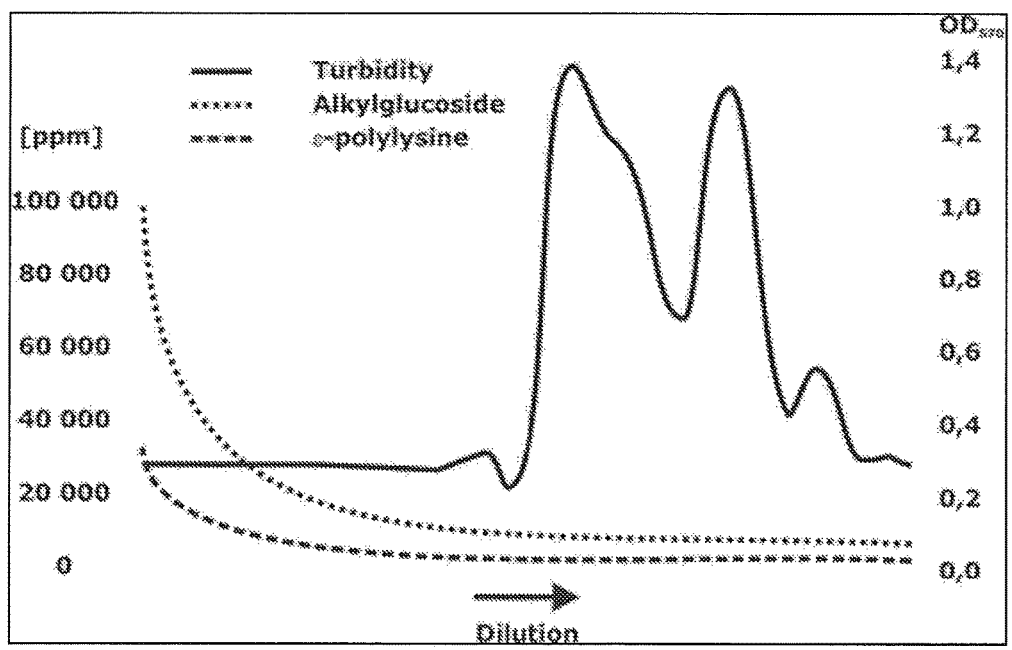
FIG. 1 shows the $O_{D570nm}$ for samples of a mixture of non-ionic surfactant (AG6210) and ε-polylysine which have been diluted from a stock mixture of 100000 ppm AG6210 and 25000 ppm ε-polylysine. Solid line: $OD_{570nm}$; short dash: ppm AG6210 in diluted mixture; long dash: ppm ε-polylysine in diluted mixture.

Crystallisation Experiments
Materials

TABLE 1

| Materials | | | |
|---|---|---|---|
| Acticide BAC 50M | Alkyl-dimethylbenzyl ammonium chloride | 68424-85-1 | Thor Specialities UK Ltd |
| Acticide DDQ 40 | Di-n-decyldimethyl ammonium chloride | 7173-51-5 | Thor Specialities UK Ltd |
| Acticide PHB 20 | Polyhexamethylene biguanide | 27083-27-8 | Thor Specialities UK Ltd |
| AG6202 | Octyl-β-D-glucopyranoside | 108081-06-7 | Akzo Nobel Surface Chemistry AB |
| AG6210 | Decyl-β-D-glucopyranoside 60% | 54549-25-6 | Akzo Nobel Surface Chemistry AB |
| | Octyl-β-D-glucopyranoside 40% | 108081-06-7 | |
| Collagentensid | Decyl-β-D-glucopyranoside | 54549-25-6 | Spinnrad GmbH |
| Decyl-β-D-glucopyranoside | | 58846-77-8 | Affymetrix UK Ltd. |
| Decyl-β-D-maltopyranoside | | 82494-09-5 | Affymetrix UK Ltd. |
| n-Heptyl-β-D-thioglucoside | | 85618-20-8 | Sigma-Aldrich Co. LLC. |
| NisinA ™ | Nisin | 1414-45-5 | Handary |
| N-nonanoyl-N-methylglucamine | | 85261-19-4 | Sigma-Aldrich Co. LLC. |
| Octyl-β-D-glucopyranoside | | 29836-26-8 | Sigma-Aldrich Co. LLC. |
| Octyl-β-D-maltopyranoside | | 82494-08-4 | Sigma-Aldrich Co. LLC. |
| Octyl-β-D-1-thioglucopyranoside | | 85618-21-9 | Sigma-Aldrich Co. LLC. |
| Lysozyme, chicken egg white | | 12650--88-3 | Sigma-Aldrich Co. LLC. |
| ε-polylysine | | 28211-04-3 | Zhengzhou Bainafo Co., Ltd. |

Methods

In general the experiments described in Examples 2 to 17 comprise two stages. First stage is the preparation of a concentrated solution of the surfactant(s) and crystal substrate in drinking water. This stage may involve the mixing of a pre-prepared stock solution(s) of the surfactant in drinking water and a pre-prepared stock solution of the substrate in drinking water. The exact procedure used is set out in each Example. The second stage is the dilution of aliquots of the stock solution with single aliquots of drinking water in glass vessels to result in diluted mixtures with varying (theoretical) concentrations of surfactant(s) and substrate as recited in the Tables of each Example. The diluted mixtures were incubated for the time and at the temperature recited in each Example before the amount of particulate matter in the mixture was assessed. This assessment was by spectrophotometer set to measure OD at a wavelength of 570 nm in Example 2 and, for Examples 3 to 17, by naked eye upon agitation of the vessel and illumination by electric light. In each of Examples 3 to 17 the following scores were given: no particles or turbidity of any sort (−); small amount of particles (+); medium amounts of particles (++); large amount of particle (+++)

Antimicrobial Efficacy Experiments

Materials

Luria Broth (LB): 10 g tryptone, 5 g yeast extract and 10 g NaCl dissolved in 1000 ml water; sterilised by autoclaving.

Neutraliser (NF): 30 ml Tween 80, 30 g saponine, 1 g histidine, 1 g cysteine dissolved in 1000 ml water; sterilised by autoclaving.

Surfactants and ε-polylysine: as above.

Method

100 μl of an *E. coli* suspension (~1.5×10$^8$ CFUs) was added to 900 μl of a freshly prepared dilute ε-polylysine/AG6210 mixture of the invention (prepared as described above) and incubated for 30 min at room temperature. Reaction was stopped by adding 9 ml of neutraliser. Mixture was then diluted 1:10 and 1:100 and 100 μl of the neat mixture and each dilution was applied to agar plates. Plates were incubated for 48 hrs at 37° C. and CFUs counted.

EXAMPLE 2

A concentrated solution of non-ionic surfactant and ε-polylysine was freshly prepared as follows: 17.8 g of AG6210 was dissolved at room temperature in a final volume of 100 ml drinking water to give a final concentration of 100000 ppm. 2.5 g of ε-polylysine was dissolved into the above mixture to give a final concentration of 25000 ppm. Corresponding concentrated solutions of non-ionic surfactant only and ε-polylysine only were prepared analogously.

Figure 1B:
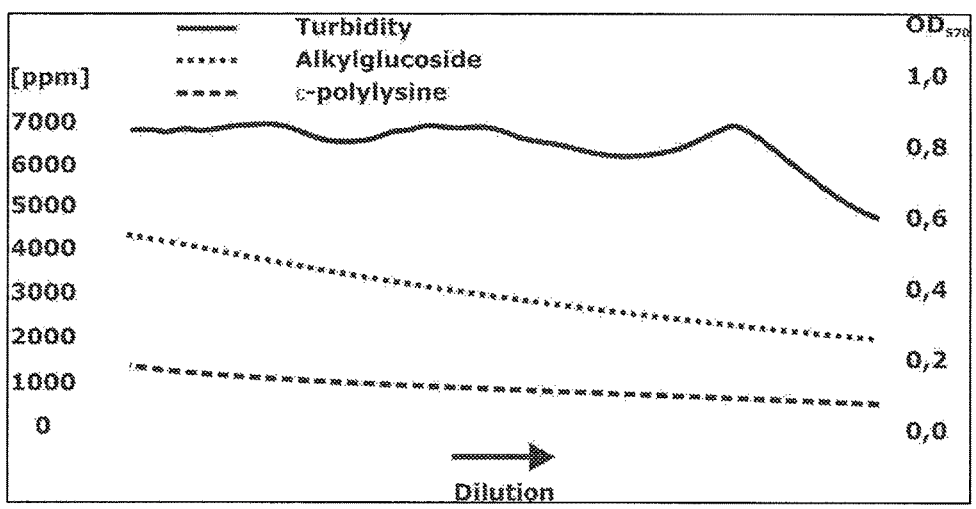
Figure 2A:
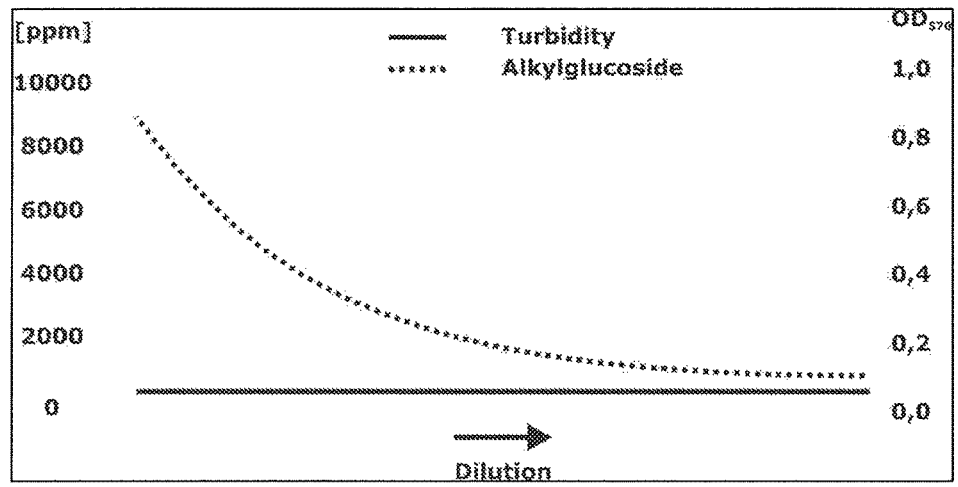
FIG. 2 shows the $O_{D570nm}$ for samples of (A) non-ionic surfactant (AG6210) which have been diluted from a stock solution of 100000 ppm AG6210 or (B) ε-polylysine which have been diluted from a stock solution of 25000 ppm ε-polylysine. Solid line: $OD_{570nm}$; short dash: ppm AG6210 in diluted mixture; long dash: ppm ε-polylysine in diluted mixture.
Figure 2B:
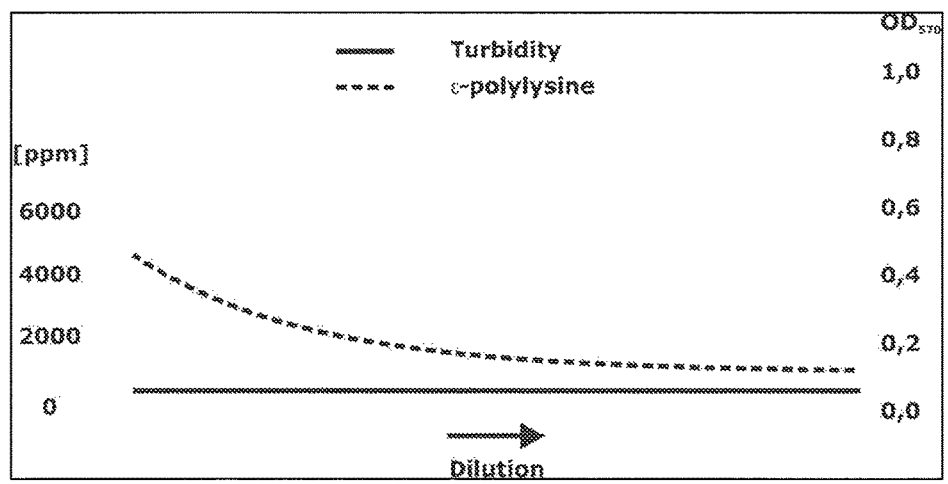

Test mixtures (100 ml) were prepared by pipetting appropriate amounts of the concentrated solution into glass flasks and adjusting the volume to 100 ml with drinking water. Mixtures were analysed immediately by measuring OD at 570 nm. Results are shown in FIGS. 1 and 2. It can been seen that sufficient dilution of concentrated mixtures of non-ionic surfactant and ε-polylysine gives rise to turbid samples and is indicative of the crystallisation process underlying the present invention. That solutions of non-ionic surfactant only or ε-polylysine only do not show turbidity upon dilution indicates the effect is a true combinatorial effect.

EXAMPLE 3

A concentrated solution of non-ionic surfactant and ε-polylysine was freshly prepared as follows: 17.8 g of AG6210 was dissolved at room temperature in a final volume of 100 ml drinking water to give a final concentration of 100000 ppm. 2.5 g of ε-polylysine was dissolved into the above mixture to give a final concentration of 25000 ppm.

Test mixtures (100 ml) were prepared by pipetting appropriate amounts of the concentrated solution into glass flasks and adjusting the volume to 100 ml with drinking water. Mixtures were stored at room temperature (~20° C.) for 2 days prior to quantification of particulate matter.

TABLE 2

Relative amounts of particulates in diluted mixtures of AG6210 and ε-polylysine. Blank entries represent combinations that were not part of experiment.

| AG6210 (ppm) | ε-polylysine | | | | | | | |
|---|---|---|---|---|---|---|---|---|
| | 0.09 mM (200 ppm) | 0.12 mM (250 ppm) | 0.16 mM (333 ppm) | 0.18 mM (400 ppm) | 0.24 mM (500 ppm) | 0.32 mM (666 ppm) | 0.48 mM (1000 ppm) | 0.72 mM (1500 ppm) |
| 400 | ++ | | | ++ | | | | |
| 500 | | +++ | | | ++ | | | |
| 666 | | | ++ | | | ++ | | |
| 800 | +++ | | | + | | | | |
| 1000* | | +++ | | | +++ | | +++ | |
| 1333 | | | ++ | | | ++ | | |
| 2000 | | | | | | | ++ | + |
| 4000 | | | | | | | ++ | + |

*n-Decyl-β-D-glucopyranoside: 3.9 mM (600 ppm); n-Octyl-β-D-glucopyranoside: 2.8 mM (400 ppm)

TABLE 3

Relative amounts of particulates in diluted mixtures of AG6210 and ε-polylysine. Blank entries represent combinations that were not part of experiment

| AG6210 (ppm) | ε-polylysine | | | | |
|---|---|---|---|---|---|
| | 0.12 mM (250 ppm) | 0.24 mM (500 ppm) | 0.6 mM (1250 ppm) | 1.2 mM (2500 ppm) | 1.8 mM (3750 ppm) |
| 250 | ++ | | | | |
| 1000* | | +++ | | | |
| 2500 | | | +++ | | |
| 5000 | | | | +++ | |
| 7500 | | | | | − |

*n-Decyl-β-D-glucopyranoside: 3.9 mM (600 ppm); n-Octyl-β-D-glucopyranoside: 2.8 mM (400 ppm)

TABLE 4

Relative amounts of particulates in diluted mixtures of AG6210 and ε-polylysine.
Blank entries represent combinations that were not part of experiment

| AG6210 (ppm) | ε-polylysine | | | | | | |
|---|---|---|---|---|---|---|---|
| | 0.09 mM (200 ppm) | 0.12 mM (250 ppm) | 0.24 mM (500 ppm) | 0.32 mM (666 ppm) | 0.36 mM (750 ppm) | 048 mM (1000 ppm) | 0.72 mM (1500 ppm) |
| 250 | | + | | | | | |
| 500 | | | +++ | | | | |
| 666 | | | | ++ | | | |
| 750 | | | | | +++ | | +++ |
| 1000* | | | | | | +++ | |
| 1333 | ++ | | | | | +++ | |
| 1500 | | | | | | | ++ |

*n-Decyl-β-D-glucopyranoside: 3.9 mM (600 ppm); n-Octyl-β-D-glucopyranoside: 2.8 mM (400 ppm)
CMC of n-decyl-β-D-glucopyranoside ($H_2O$, 20° C.): 2.2 mM, approx. 330 ppm
CMC of n-octyl-β-D-glucopyranoside ($H_2O$, 20° C.): 19 mM, approx. 2800 ppm

EXAMPLE 4

Stock solutions were freshly prepared as follows:

n-Decyl-β-D-glucopyranoside: 10 g was added to 100 ml $H_2O$ to give a concentration of 100000 ppm (0.322 μMol/μl).

n-Octyl-β-D-glucopyranoside: 10 g was added 100 ml $H_2O$ to give a concentration of 100000 ppm (0.350 μMol/μl)

ε-polylysine (PPL) 5 g was added to 100 ml of $H_2O$ to give a concentration of 50000 ppm (0.012 μMol/μl)

Mixing Procedure:

1. xxx μl of n-octyl-β-D-glucopyranoside stock solution was pipetted to 100 ml glass bottle.
2. yyy μl of n-decyl-β-D-glucopyranoside stock solution were added to the bottle.
3. 1 ml of drinking water was added and liquids were mixed by gentle shaking.
4. 100 μl of ε-polylysine (PPL) stock solution was added to the above premix and liquids were mixed by gentle shaking.
5. Finally, bottles were filled with drinking water to a final volume of 50 ml.
6. Mixtures were incubated at room temperature (~20° C.) and stored at room temperature until quantification of particulate matter at 24, 72, 500 and 668 hrs.

Figure 3:
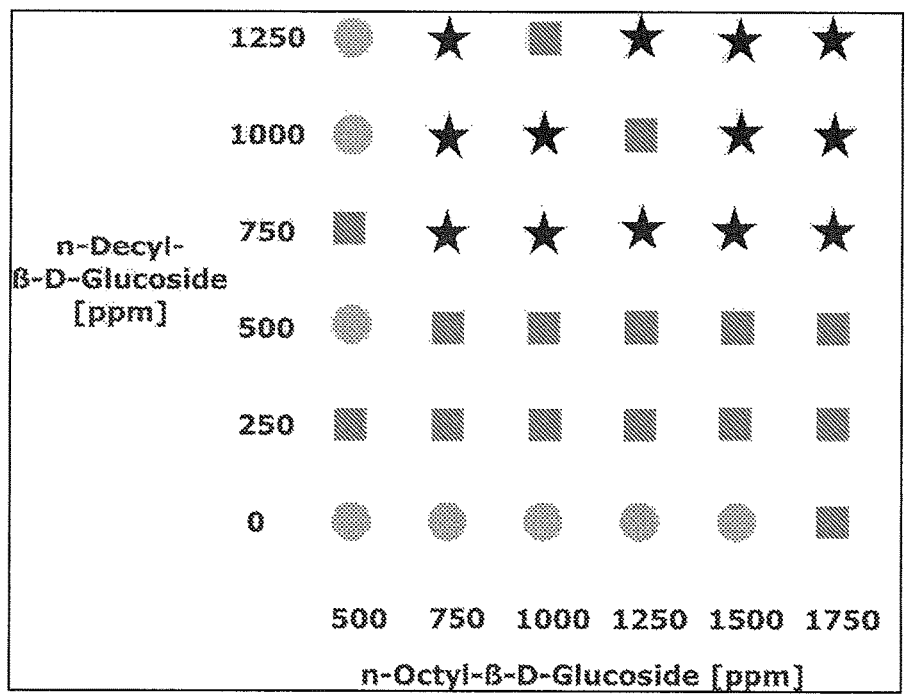
FIG. 3 shows the mean average of the amount of crystals seen over eight timepoints (1, 5, 8, 12, 15, 24, 42 and 49 days) for various dilutions from a stock mixture of 100000 ppm AG6210 and 25000 ppm ε-polylysine. Circle: small amounts of crystals; square: medium amounts of crystals; star: large amounts of crystals.

Tables 5 and 6 show the results at 24 hr and 72 hr. FIG. 3 displays the mean average of the amount of crystals seen over the four timepoints for each dilution

TABLE 5

Relative amounts of particulates in diluted mixtures of n-decyl-β-D-glucopyranoside, n-octyl-β-D-glucopyranoside and ε-polylysine (at 11.6 μMol/232 μM/500 ppm) after 24 hrs.

| n-Decyl-β-D-glucopyranoside | | | | n-Octyl-β-D-glucopyranoside | | | | | | |
|---|---|---|---|---|---|---|---|---|---|---|
| | | | | 175 | 262 | 350 | 437 | 525 | 612 | μMol |
| | | | | 3.50 | 5.24 | 7.00 | 9.40 | 10.50 | 12.24 | mM |
| | | | | 500 | 750 | 1000 | 1250 | 1500 | 1750 | ppm |
| μMol | mM | ppm | x CMC | 0.009 | 0.014 | 0.018 | 0.023 | 0.027 | 0.032 | x CMC |
| 0 | 0 | 0 | 0 | + | + | + | + | + | ++ | |
| 80.5 | 1.61 | 250 | 0.73 | ++ | ++ | ++ | ++ | ++ | ++ | |
| 161.0 | 3.22 | 500 | 1.46 | + | ++ | ++ | + | + | ++ | |
| 241.5 | 4.83 | 750 | 2.20 | ++ | + | ++ | ++ | + | ++ | |
| 322.0 | 6.44 | 1000 | 2.93 | + | + | ++ | + | ++ | + | |
| 402.5 | 8.05 | 1250 | 3.66 | + | + | ++ | + | + | ++ | |

TABLE 6

Relative amounts of particulates in diluted mixtures of n-decyl-β-D-glucopyranoside, n-octyl-β-D-glucopyranoside and ε-polylysine (at 11.6 μMol/232 μM/500 ppm) after 72 hrs.

| n-Decyl-β-D-glucopyranoside | | | | n-octyl-β-D-glucopyranoside | | | | | | |
|---|---|---|---|---|---|---|---|---|---|---|
| | | | | 175 | 262 | 350 | 437 | 525 | 612 | μMol |
| | | | | 3.50 | 5.24 | 7.00 | 9.40 | 10.50 | 12.24 | mM |
| | | | | 500 | 750 | 1000 | 1250 | 1500 | 1750 | ppm |
| μMol | mM | ppm | x CMC | 0.009 | 0.014 | 0.018 | 0.023 | 0.027 | 0.032 | x CMC |
| 0 | 0 | 0 | 0 | + | + | + | + | + | + | |
| 80.5 | 1.61 | 250 | 0.73 | ++ | ++ | ++ | ++ | ++ | + | |

TABLE 6-continued

Relative amounts of particulates in diluted mixtures of n-decyl-β-D-glucopyranoside, n-octyl-β-D-glucopyranoside and ε-polylysine (at 11.6 μMol/232 μM/500 ppm) after 72 hrs.

| | | | | n-octyl-β-D-glucopyranoside | | | | | |
|---|---|---|---|---|---|---|---|---|---|
| | | | | 175 | 262 | 350 | 437 | 525 | 612 μMol |
| | | | | 3.50 | 5.24 | 7.00 | 9.40 | 10.50 | 12.24 mM |
| n-Decyl-β-D-glucopyranoside | | | | 500 | 750 | 1000 | 1250 | 1500 | 1750 ppm |
| μMol | mM | ppm | x CMC | 0.009 | 0.014 | 0.018 | 0.023 | 0.027 | 0.032 x CMC |
| 161.0 | 3.22 | 500 | 1.46 | + | ++ | ++ | + | ++ | + |
| 241.5 | 4.83 | 750 | 2.20 | ++ | ++ | ++ | ++ | ++ | ++ |
| 322.0 | 6.44 | 1000 | 2.93 | + | ++ | ++ | ++ | ++ | ++ |
| 402.5 | 8.05 | 1250 | 3.66 | ++ | ++ | ++ | ++ | ++ | ++ |

CMC of n-decyl-β-D-glucopyranoside (H₂O, 20° C.): 2.2 mM, approx. 330 ppm
CMC of n-octyl-β-D-glucopyranoside (H₂O, 20° C.): 19 mM, approx. 2800 ppm

EXAMPLE 5

A concentrated solution of non-ionic surfactant and ε-polylysine was freshly prepared as follows: 17.8 g of AG6210 was dissolved at room temperature in a final volume of 100 ml drinking water to give a final concentration of 100000 ppm. 2.5 g of ε-polylysine was dissolved into the above mixture to give a final concentration of 25000 ppm.

Test mixtures (50 ml) were prepared by diluting defined amounts of the concentrated solution with water to a final volume of 50 ml. Mixtures were stored at room temperature (~20° C.) for the time shown prior to quantification of particulate matter. Results are shown in Table 7.

Figure 4:
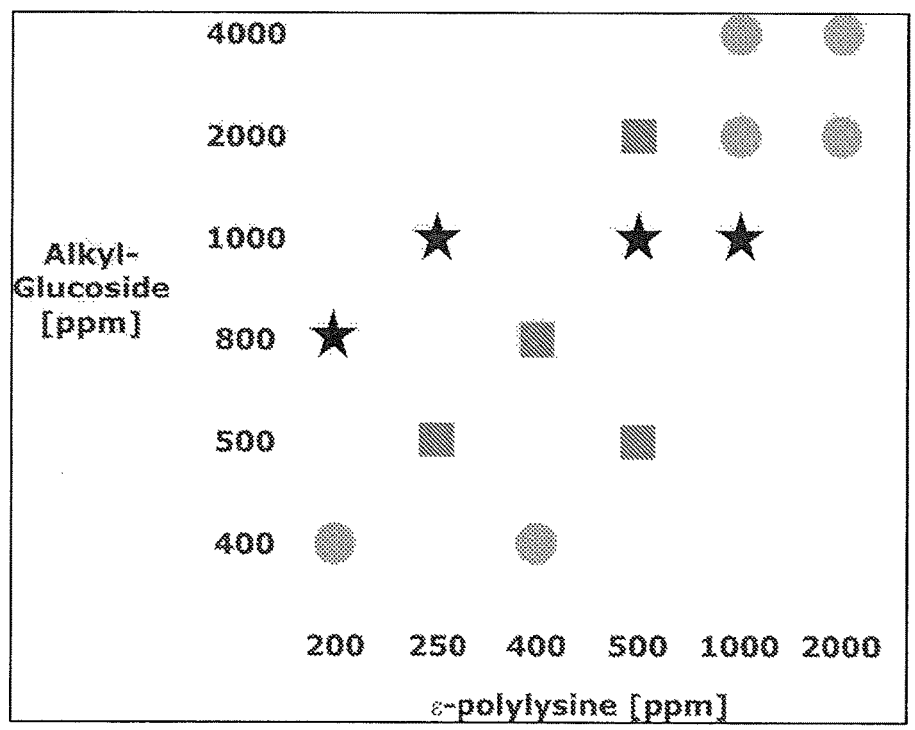
FIG. 4 shows the mean average of the amount of crystals seen over eight timepoints (1, 5, 8, 12, 15, 24, 42 and 49 days) for various dilutions from a stock mixture of 100000 ppm AG6210 and 25000 ppm ε-polylysine. Circle: small amounts of crystals; square: medium amounts of crystals; star: large amounts of crystals.

FIG. 4 combines the results of this experiment with those of Examples 6-8 and displays the mean average of the amount of crystals seen over the eight timepoints for each dilution.

TABLE 7

Relative amounts of particulates in diluted mixtures of AG6210 and ε-polylysine after varying incubation times. Dilution from concentrated solution of 100000 ppm AG6210 & 25000 ppm ε-polylysine

| | n-Decyl-β-D-glucopyranoside (mM) | 15.4 | 7.7 | 3.9 | 3.1 |
|---|---|---|---|---|---|
| | (ppm) | 2400 | 1200 | 600 | 480 |
| | n-Octyl-β-D-glucopyranoside (mM) | 11.2 | 5.6 | 2.8 | 2.2 |
| | (ppm) | 1600 | 800 | 400 | 320 |
| | ε-polylysine (mM) | 0.46 | 0.23 | 0.12 | 0.09 |
| Day | (ppm) | 1000 | 500 | 250 | 200 |
| 1 | | + | + | ++ | + |
| 5 | | + | ++ | +++ | +++ |
| 8 | | + | + | +++ | ++ |
| 12 | | + | + | +++ | +++ |
| 15 | | + | ++ | +++ | ++ |
| 24 | | + | ++ | +++ | +++ |
| 42 | | + | ++ | +++ | +++ |
| 49 | | ++ | +++ | +++ | +++ |

CMC of n-decyl-β-D-glucopyranoside (H₂O, 20° C.): 2.2 mM, approx. 330 ppm
CMC of n-octyl-β-D-glucopyranoside (H₂O, 20° C.): 19 mM, approx. 2800 ppm

EXAMPLE 6

A concentrated solution of non-ionic surfactant and ε-polylysine was freshly prepared as follows: 17.8 g of AG6210 was dissolved at room temperature in a final volume of 100 ml drinking water to give a final concentration of 100000 ppm. 5 g of ε-polylysine was dissolved into the above mixture to give a final concentration of 50000 ppm.

Test mixtures (50 ml) were prepared by diluting defined amounts of the concentrated solution with water to a final volume of 50 ml. Mixtures were stored at room temperature (~20° C.) for the time shown prior to quantification of particulate matter. Results are shown in Table 8.

FIG. 4 combines the results of this experiment with those of Examples 5, 7 and 8 and displays the mean average of the amount of crystals seen over the eight timepoints for each dilution.

TABLE 8

Relative amounts of particulates in diluted mixtures of AG6210 and ε-polylysine after varying incubation times. Dilution from concentrated solution of 100000 ppm AG6210 and 50000 ppm ε-polylysine

| | n-Decyl-β-D-glucopyranoside (mM) | 15.4 | 7.7 | 3.9 | 3.1 |
|---|---|---|---|---|---|
| | (ppm) | 2400 | 1200 | 600 | 480 |
| | n-Octyl-β-D-glucopyranoside (mM) | 11.2 | 5.6 | 2.8 | 2.2 |
| | (ppm) | 1600 | 800 | 400 | 320 |
| | ε-polylysine (mM) | 0.92 | 0.46 | 0.24 | 0.18 |
| Day | (ppm) | 2000 | 1000 | 500 | 400 |
| 1 | | ++ | + | ++ | + |
| 5 | | + | + | +++ | ++ |
| 8 | | + | + | +++ | ++ |
| 12 | | + | + | +++ | ++ |
| 15 | | + | ++ | +++ | +++ |
| 24 | | ++ | ++ | ++ | ++ |
| 42 | | + | ++ | +++ | +++ |
| 49 | | + | ++ | +++ | +++ |

CMC of n-decyl-β-D-glucopyranoside (H₂O, 20° C.): 2.2 mM, approx. 330 ppm
CMC of n-octyl-β-D-glucopyranoside (H₂O, 20° C.): 19 mM, approx. 2800 ppm

EXAMPLE 7

A concentrated solution of non-ionic surfactant and ε-polylysine was freshly prepared as follows: 8.9 g of AG6210 was dissolved at room temperature in a final volume of 100 ml drinking water to give a final concentration of 50000 ppm. 2.5 g of ε-polylysine was dissolved into the above mixture to give a final concentration of 25000 ppm.

Test mixtures (50 ml) were prepared by diluting defined amounts of the concentrated solution with water to a final volume of 50 ml. Mixtures were stored at room temperature (~20° C.) for the time shown prior to quantification of particulate matter. Results are shown in Table 9.

FIG. 4 combines the results of this experiment with those of Examples 5, 6 and 8 and displays the mean average of the amount of crystals seen over the eight timepoints for each dilution.

TABLE 9

Relative amounts of particulates in diluted mixtures of AG6210 and ε-polylysine after varying incubation times. Dilution from concentrated solution of 50000 ppm AG6210 and 25000 ppm ε-polylysine

|  |  |  |  |  |  |
|---|---|---|---|---|---|
| n-Decyl-β-D-glucopyranoside (mM) |  | 7.7 | 3.8 | 1.9 | 1.5 |
|  | (ppm) | 1200 | 600 | 300 | 240 |
| n-Octyl-β-D-glucopyranoside (mM) |  | 5.6 | 2.8 | 1.4 | 1.1 |
|  | (ppm) | 800 | 400 | 200 | 160 |
| ε-polylysine (mM) |  | 0.46 | 0.23 | 0.12 | 0.09 |
| Day | (ppm) | 1000 | 500 | 250 | 200 |
| 1 |  | + | ++ | + | + |
| 5 |  | + | +++ | +++ | ++ |
| 8 |  | + | +++ | ++ | + |
| 12 |  | + | +++ | ++ | + |
| 15 |  | ++ | +++ | ++ | + |
| 24 |  | ++ | +++ | ++ | + |
| 42 |  | + | ++ | +++ | + |
| 49 |  | + | + | ++ | + |

CMC of n-decyl-β-D-glucopyranoside (H₂O, 20° C.): 2.2 mM, approx. 330 ppm
CMC of n-octyl-β-D-glucopyranoside (H₂O, 20° C.): 19 mM, approx. 2800 ppm

EXAMPLE 8

A concentrated solution of non-ionic surfactant and ε-polylysine was freshly prepared as follows: 8.9 g of AG6210 was dissolved at room temperature in a final volume of 100 ml drinking water to give a final concentration of 50000 ppm. 5 g of ε-polylysine was dissolved into the above mixture to give a final concentration of 50000 ppm.

Test mixtures (50 ml) were prepared by diluting defined amounts of the concentrated solution with water to a final volume of 50 ml. Mixtures were stored at room temperature (~20° C.) for the time shown prior to quantification of particulate matter. Results are shown in Table 10.

FIG. 4 combines the results of this experiment with those of Examples 5-7 and displays the mean average of the amount of crystals seen over the eight timepoints for each dilution.

TABLE 10

Relative amounts of particulates in diluted mixtures of AG6210 and ε-polylysine after varying incubation times. Dilution from concentrated solution of 50000 ppm AG6210 and 50000 ppm ε-polylysine

|  |  |  |  |  |  |
|---|---|---|---|---|---|
| n-Decyl-β-D-glucopyranoside (mM) |  | 7.7 | 3.8 | 1.9 | 1.5 |
|  | (ppm) | 1200 | 600 | 300 | 240 |
| n-Octyl-β-D-glucopyranoside (mM) |  | 5.6 | 2.8 | 1.4 | 1.1 |
|  | (ppm) | 800 | 400 | 200 | 160 |
| ε-polylysine (mM) |  | 0.92 | 0.46 | 0.24 | 0.18 |
| Day | (ppm) | 2000 | 1000 | 500 | 400 |
| 1 |  | + | ++ | ++ | + |
| 5 |  | + | ++ | ++ | + |
| 8 |  | + | ++ | +++ | + |
| 12 |  | + | +++ | ++ | + |
| 15 |  | + | +++ | ++ | + |
| 24 |  | ++ | +++ | +++ | + |
| 42 |  | + | +++ | ++ | ++ |
| 49 |  | ++ | +++ | ++ | ++ |

CMC of n-decyl-β-D-glucopyranoside (H₂O, 20° C.): 2.2 mM, approx. 330 ppm
CMC of n-octyl-β-D-glucopyranoside (H₂O, 20° C.): 19 mM, approx. 2800 ppm

EXAMPLE 9

Stock solutions were freshly prepared as follows:
9.45 g of 53% n-decyl-β-D-glucopyranoside (Collagentensid, Spinnrad GmbH) was dissolved in 50 ml drinking water to give 100000 ppm.

7.7 g of 65% n-octyl-β-D-glucopyranoside (AG 6202, Akzo Nobel) was dissolved in 50 ml drinking water to give 100000 ppm.

5.0 g of ε-polylysine (Zhengzhou Bainafo Bioengineering Co., Ltd.) was dissolved in 50 ml drinking water to give 100000 ppm.

Mixing Procedure:

Test mixtures marked in bold were prepared by pipetting appropriate μl amounts of stock solutions (for each ppm of the final concentration shown 1 μl of stock solution was used) into 100 ml glass bottles which were then filled with drinking water to a final volume of 100 ml. The other mixtures were prepared by appropriate dilution of a pre-mixed combination of stock solutions with drinking water to a final volume of 20 ml in glass bottles. The test mixtures were mixed by gentle shaking and stored at room temperature for 72 hrs and then quantification of particulate matter took place. The mixtures were agitated daily by gentle shaking. Results are shown in Table 11.

TABLE 11

Relative amounts of particulates in diluted mixtures of n-decyl-β-D-glucopyranoside, n-octyl-β-D-glucopyranoside and ε-polylysine after 72 hrs.

| n-Decyl-β-D-glucopyranoside | | n-Octyl-β-D-glucopyranoside | | ε-polylysine (PPL) | | |
|---|---|---|---|---|---|---|
| (ppm) | (mM) | (ppm) | (mM) | (ppm) | (mM) | Crystals |
| 3000 | 9.66 | 1000 | 7.0 | 2000 | 0.84 | + |
| 1500 | 9.66 | 500 | 3.5 | 1000 | 0.42 | ++ |
| 1000 | 6.44 | 333 | 2.3 | 666 | 0.28 | ++ |
| 750 | 4.8 | 250 | 1.7 | 500 | 0.21 | +++ |
| 600 | 3.8 | 200 | 1.4 | 400 | 0.17 | + |
| 2000 | 12.88 | 2000 | 14 | 2000 | 0.84 | + |
| 1000 | 6.44 | 1000 | 7.0 | 1000 | 0.42 | +++ |
| 666 | 4.3 | 666 | 4.7 | 666 | 0.28 | ++ |
| 500 | 3.22 | 500 | 3.5 | 500 | 0.21 | ++ |
| 400 | 5.5 | 400 | 2.8 | 400 | 0.17 | + |
| 1000 | 6.44 | 3000 | 21 | 2000 | 0.84 | ++ |
| 500 | 3.22 | 1500 | 10.5 | 1000 | 0.42 | ++ |
| 333 | 2.1 | 1000 | 7.0 | 666 | 0.28 | ++ |
| 250 | 1.6 | 750 | 5.2 | 500 | 0.21 | ++ |
| 200 | 2.7 | 600 | 4.2 | 400 | 0.17 | ++ |
| 0 | 0 | 2000 | 14 | 1000 | 0.42 | ++ |
| 0 | 0 | 1333 | 9.3 | 666 | 0.28 | + |
| 0 | 0 | 1000 | 7.0 | 500 | 0.21 | + |
| 0 | 0 | 800 | 5.6 | 400 | 0.17 | + |

CMC of n-decyl-β-D-glucopyranoside (H₂O, 20° C.): 2.2 mM, approx. 330 ppm
CMC of n-octyl-β-D-glucopyranoside (H₂O, 20° C.): 19 mM, approx. 2800 ppm

EXAMPLE 10

100000 ppm stock solutions of each surfactant were freshly prepared by dissolving 1 g of surfactant in 10 ml of drinking water.

100000 ppm stock solution of ε-polylysine was prepared by dissolving 5 g of ε-polylysine in 50 ml drinking water.

Appropriate amounts of stock solutions were added to a 50 ml glass bottle and mixed by shaking. Test mixture volume was then adjusted to 50 ml with drinking water. Glass bottles were stored at room temperature (~20° C.) for 48 hrs and then quantification of particulate matter took place.

TABLE 12

Relative amounts of particulates in diluted mixtures of n-decyl-β-D-maltopyranoside, n-octyl-β-D-maltopyranoside and ε-polylysine after 48 hrs.

| n-Decyl-β-D-maltopyranoside (mM) (ppm) | n-Octyl-β-D-maltopyranoside (mM) (ppm) | ε-polylysine (mM) (ppm) | Crystals |
|---|---|---|---|
| 20.1 | 18.9 | 0.84 | + |
| 2000 | 2000 | 2000 | |
| 10 | 9.4 | 0.42 | + |
| 1000 | 1000 | 1000 | |
| 5 | 4.7 | 0.21 | + |
| 500 | 500 | 500 | |
| 4 | 3.8 | 0.17 | + |
| 400 | 400 | 400 | |

CMC (H$_2$O, 20° C.) of n-decyl-β-D-maltopyranoside: 1.6 mM
CMC (H$_2$O, 20° C.) of n-octyl-β-D-maltopyranoside: 23 mM

TABLE 13

Relative amounts of particulates in diluted mixtures of n-decyl-β-D-glucopyranoside, n-octyl-β-D-maltopyranoside and ε-polylysine after 48 hrs.

| n-Decyl-β-D-glucopyranoside (mM) (ppm) | n-Octyl-β-D-maltopyranoside (mM) (ppm) | ε-polylysine (mM) (ppm) | Crystals |
|---|---|---|---|
| 12.9 | 18.9 | 0.84 | ++ |
| 2000 | 2000 | 2000 | |
| 6.4 | 9.4 | 0.42 | ++ |
| 1000 | 1000 | 1000 | |
| 5.2 | 7.5 | 0.34 | + |
| 800 | 800 | 800 | |
| 4.3 | 6.3 | 0.28 | + |
| 666 | 666 | 666 | |
| 3.2 | 4.7 | 0.21 | ++ |
| 500 | 500 | 500 | |
| 2.6 | 3.8 | 0.17 | ++ |
| 400 | 400 | 400 | |

CMC (H$_2$O, 20° C.) of n-decyl-β-D-glucopyranoside: 2.2 mM
CMC (H$_2$O, 20° C.) of n-octyl-β-D-maltopyranoside: 23 mM

TABLE 14

Relative amounts of particulates in diluted mixtures of n-decyl-β-D-maltopyranoside, n-octyl-β-D-glucopyranoside and ε-polylysine after 48 hrs.

| n-Decyl-β-D-maltopyranoside (mM) (ppm) | n-Octyl-β-D-glucopyranoside (mM) (ppm) | ε-polylysine (mM) (ppm) | Crystals |
|---|---|---|---|
| 10 | 7 | 0.42 | + |
| 1000 | 1000 | 1000 | |
| 6.7 | 4.7 | 0.28 | + |
| 666 | 666 | 666 | |
| 5 | 3.5 | 0.21 | − |
| 500 | 500 | 500 | |
| 4 | 2.8 | 0.17 | − |
| 400 | 400 | 400 | |

CMC (H$_2$O, 20° C.) of n-decyl-β-D-maltopyranoside: 1.6 mM
CMC (H$_2$O, 20° C.) of n-octyl-β-D-glucopyranoside: 19 mM

TABLE 15

Relative amounts of particulates in diluted mixtures of n-heptyl-β-D-thioglucoside, n-octyl-β-D-glucopyranoside and ε-polylysine after 48 hrs.

| n-Heptyl-β-D-thioglucoside (mM) (ppm) | n-octyl-β-D-glucopyranoside (mM) (ppm) | ε-polylysine (mM) (ppm) | Crystals |
|---|---|---|---|
| 6.8 | 7 | 0.42 | +/− |
| 1000 | 1000 | 1000 | |
| 4.5 | 4.7 | 0.28 | +/− |
| 666 | 666 | 666 | |
| 3.4 | 3.5 | 0.21 | ++ |
| 500 | 500 | 500 | |
| 2.7 | 2.8 | 0.17 | +/− |
| 400 | 400 | 400 | |

CMC (H$_2$O, 20° C.) of n-heptyl-β-D-thioglucoside: 29 mM
CMC (H$_2$O, 20° C.) of n-octyl-β-D-glucopyranoside: 19 mM

TABLE 16

Relative amounts of particulates in diluted mixtures of n-heptyl-β-D-thioglucoside, n-decyl-β-D-maltopyranoside and ε-polylysine after 48 hrs.

| n-Heptyl-β-D-thioglucoside (mM) (ppm) | n-Decyl-β-D-maltopyranoside (mM) (ppm) | ε-polylysine (mM) (ppm) | Crystals |
|---|---|---|---|
| 13.6 | 20 | 0.84 | ++ |
| 2000 | 2000 | 2000 | |
| 6.8 | 10 | 0.42 | ++ |
| 1000 | 1000 | 1000 | |
| 4.5 | 6.7 | 0.42 | + |
| 666 | 666 | 1000 | |
| 3.4 | 5 | 0.21 | + |
| 500 | 500 | 500 | |
| 2.7 | 4 | 0.17 | + |
| 400 | 400 | 400 | |

CMC (H$_2$O, 20° C.) of n-heptyl-β-D-thioglucoside: 29 mM
CMC (H$_2$O, 20° C.) of n-decyl-β-D-maltopyranoside: 1.6 mM

TABLE 17

Relative amounts of particulates in diluted mixtures of n-decyl-β-D-glucopyranoside, n-nonanoyl-N-methylglucamine and ε-polylysine after 48 hrs.

| n-Decyl-β-D-glucopyranoside (mM) (ppm) | n-Nonanoyl-N-methylglucamine (mM) (ppm) | ε-polylysine (mM) (ppm) | Crystals |
|---|---|---|---|
| 6.5 | 6.8 | 0.42 | ++ |
| 1000 | 1000 | 1000 | |
| 4.3 | 4.5 | 0.42 | + |
| 666 | 666 | 1000 | |
| 3.25 | 3.4 | 0.21 | +++ |
| 500 | 500 | 500 | |
| 2.6 | 2.7 | 0.17 | + |
| 400 | 400 | 400 | |

CMC (H$_2$O, 20° C.) of n-nonanoyl-N-methylglucamine: 19-25 mM
CMC (H$_2$O, 20° C.) of n-decyl-β-D-glucopyranoside: 2.2 mM

TABLE 18

Relative amounts of particulates in dilute mixtures of n-decyl-β-D-maltopyranoside, n-nonanoyl-N-methylglucamine and ε-polylysine after 48 hrs.

| n-Decyl-β-D-maltopyranoside (mM) (ppm) | n-Nonanoyl-N-methylglucamine (mM) (ppm) | ε-polylysine (mM) (ppm) | Crystals |
|---|---|---|---|
| 10<br>1000 | 6.8<br>1000 | 0.42<br>1000 | + |
| 6.7<br>666 | 4.5<br>666 | 0.42<br>1000 | + |
| 5<br>500 | 3.4<br>500 | 0.21<br>500 | ++ |
| 4<br>400 | 2.7<br>400 | 0.17<br>400 | + |

CMC ($H_2O$, 20° C.) of n-decyl-β-D-maltopyranoside: 1.6 mM
CMC ($H_2O$, 20° C.) of N-nonanoyl-N-methylglucamine: 19-25 mM

EXAMPLE 11

A concentrated solution of n-octyl-β-D-glucopyranoside (non-ionic surfactant), alkyl-dimethylbenzyl ammonium chloride (quaternary ammonium cationic surfactant) and ε-polylysine was freshly prepared by combining 10 ml of 50% alkyl-dimethylbenzyl ammonium chloride (Acticide; BAC 50M solution; Thor Specialities UK Ltd), 7.7 ml of 65% n-octyl-β-D-glucopyranoside (AG 6202; Akzo Nobel), 1.25 g ε-polylysine (Zhengzhou Bainafo Bioengineering Co., Ltd.) and 82.3 ml of drinking water Test mixtures were prepared by diluting appropriate amounts of the concentrated solution with water to achieve the concentrations of the various components shown in the following Table. Mixtures were stored at room temperature (~20° C.) for the time shown prior to quantification of particulate matter.

TABLE 19

Relative amounts of particulates in diluted mixtures of n-octyl-β-D-glucopyranoside, alkyl-dimethylbenzyl ammonium chloride and ε-polylysine after varying incubation times.

| alkyl-dimethylbenzyl ammonium chloride (ppm) | n-octyl-β-D-glucopyranoside (ppm) | ε-polylysine (ppm) | Crystallization | | | | | |
|---|---|---|---|---|---|---|---|---|
| | | | 1 day | 7 day | 14 day | 21 day | 28 day | 35 day |
| 400 | 400 | 100 | + | + | + | ++ | ++ | + |
| 500 | 500 | 125 | + | + | ++ | ++ | ++ | + |
| 1000 | 1000 | 250 | + | ++ | ++ | ++ | ++ | + |
| 2000 | 2000 | 500 | + | ++ | ++ | + | + | + |

CMC of alkyl-dimethylbenzyl ammonium chloride ($H_2O$, 20° C.): 0.7 mM, approx. 0.257 ppm when average molecular weight is 368.
CMC of n-octyl-β-D-glucopyranoside ($H_2O$, 20° C.): 19 mM, approx. 2800 ppm

EXAMPLE 12

A concentrated solution of n-octyl-β-D-glucopyranoside (non-ionic surfactant), di-n-decyldimethyl ammonium chloride (quaternary ammonium cationic surfactant) and ε-polylysine was freshly prepared by combining 12.5 ml of a 40% decyldimethyl ammonium chloride (Acticide; DDQ 40 solution, Thor Specialities UK Ltd), 7.7 ml of 65% n-octyl-β-D-glucopyranoside (AG 6202; Akzo Nobel), 1.25 g ε-polylysine (Zhengzhou Bainafo Bioengineering Co., Ltd.) and 78.55 ml of drinking water Test mixtures were prepared by diluting appropriate amounts of the concentrated solution with water to achieve the concentrations of the various components shown in the following Table. Mixtures were stored at room temperature (~20° C.) for the time shown prior to quantification of particulate matter.

TABLE 20

Relative amounts of particulates in diluted mixtures of n-octyl-β-D-glucopyranoside, di-n-decyldimethyl ammonium chloride and ε-polylysine after varying incubation times.

| di-n-decyldimethyl ammonium chloride (ppm) | n-octyl-β-D-glucopyranoside (ppm) | ε-polylysine (ppm) | Crystallisation | | | | | |
|---|---|---|---|---|---|---|---|---|
| | | | 1 day | 7 day | 14 day | 21 day | 28 day | 35 day |
| 400 | 400 | 100 | + | + | ++ | + | + | ++ |
| 500 | 500 | 125 | + | + | ++ | + | ++ | ++ |
| 1000 | 1000 | 250 | + | ++ | + | + | ++ | ++ |
| 2000 | 2000 | 500 | ++ | ++ | + | + | + | ++ |

CMC of di-n-decyldimethyl ammonium chloride ($H_2O$, 20° C.): 1.5 mM, approx. 0.543 ppm when average molecular weight is 363.
CMC of n-octyl-β-D-glucopyranoside ($H_2O$, 20° C.): 19 mM, approx. 2800 ppm

EXAMPLE 13

A concentrated solution of non-ionic surfactant and lysozyme was freshly prepared as follows: 17.8 g of AG6210 was dissolved at room temperature in a final volume of 100 ml drinking water to give a final concentration of 100000 ppm. 5 g of lysozyme was dissolved into the above mixture to give a final concentration of 50000 ppm.

Test mixtures (50 ml) were prepared by diluting appropriate amounts of the concentrated solution with water to make a final volume of 50 ml. Mixtures were stored at room temperature (~20° C.) for 24 hrs prior to quantification of particulate matter.

TABLE 21

Relative amounts of particulates in diluted mixtures of AG6210 and lysozyme.

| APG (ppm) | Lysozyme (ppm) | Crystallisation |
| --- | --- | --- |
| 500 | 500 | − |
| 1000 | 500 | + |
| 1250 | 500 | ++ |
| 2000 | 1000 | +++ |
| 2500 | 1250 | +++ |
| 3000 | 1500 | +++ |
| 5000 | 2500 | +++ |
| 7500 | 3750 | ++ |
| 10000 | 5000 | − |

CMC of n-decyl-β-D-glucopyranoside ($H_2O$, 20° C.): 2.2 mM, approx. 330 ppm
CMC of n-octyl-β-D-glucopyranoside ($H_2O$, 20° C.): 19 mM, approx. 2800 ppm

EXAMPLE 14

A concentrated solution of non-ionic surfactant and polyhexamethylene biguanide (PHMB) was freshly prepared as follows: 17.8 g of AG6210 was dissolved at room temperature in a final volume of 100 ml drinking water to give a final concentration of 100000 ppm. 50 ml of PHMB (Acticide PHB 20, Thor Specialities UK Ltd) was dissolved into the above mixture to give a final concentration of 100000 ppm Test mixtures (50 ml) were prepared by diluting appropriate amounts of the concentrated solution with water to make a final volume of 50 ml. Mixtures were stored at room temperature (~20° C.) for 24 hrs prior to quantification of particulate matter.

TABLE 22

Relative amounts of particulates in diluted mixtures of AG6210 and PHMB.

| APG (ppm) | Polyhexamethylene biguanide (ppm) | Crystallization |
| --- | --- | --- |
| 500 | 500 | ++ |
| 1000 | 1000 | +++ |
| 2500 | 2500 | +++ |
| 5000 | 5000 | + |

CMC of n-decyl-β-D-glucopyranoside ($H_2O$, 20° C.): 2.2 mM, approx. 330 ppm
CMC of n-octyl-β-D-glucopyranoside ($H_2O$, 20° C.): 19 mM, approx. 2800 ppm

EXAMPLE 15

Stock solutions were freshly prepared as follows:
n-Decyl-β-D-glucopyranoside: 10 g was added to 100 ml $H_2O$ to give a concentration of 100000 ppm
n-Octyl-β-D-glucopyranoside: 10 g was added 100 ml $H_2O$ to give a concentration of 100000 ppm
PHMB: 5 g was added to 100 ml of $H_2O$ to give a concentration of 50000 ppm Mixing Procedure:
1. xxx µl of n-octyl-β-D-glucopyranoside stock solution was pipetted to 100 ml glass bottle.
2. yyy µl of n-decyl-β-D-glucopyranoside stock solution were added to the bottle.
3. 1 ml of drinking water was added and liquids were mixed by gentle shaking.
4. zzz µl of PHMB stock solution was added to the above premix and liquids were mixed by gentle shaking.
5. Finally, bottles were filled with drinking water to a final volume of 50 ml.
6. Mixtures were incubated at room temperature (~20° C.) and stored at room temperature for 24 hrs until quantification of particulate matter.

TABLE 23

Relative amounts of particulates in diluted mixtures of n-decyl-β-D-glucopyranoside, n-octyl-β-D-glucopyranoside and PHMB.

| n-Decyl-β-D-glucopyranoside (ppm) | n-octyl-β-D-glucopyranoside (ppm) | Polyhexamethylene biguanide (ppm) | Crystallization |
| --- | --- | --- | --- |
| 500 | 500 | 500 | − |
| 1000 | 1000 | 1000 | +++ |
| 2500 | 2500 | 2500 | +++ |
| 5000 | 5000 | 5000 | − |

CMC of n-decyl-β-D-glucopyranoside ($H_2O$, 20° C.): 2.2 mM, approx. 330 ppm
CMC of n-octyl-β-D-glucopyranoside ($H_2O$, 20° C.): 19 mM, approx. 2800 ppm

EXAMPLE 16

Stock solutions were freshly prepared as follows:
n-Decyl-β-D-glucopyranoside: 5.68 ml of a 53% n-decyl-β-D-glucopyranoside solution (Collagentensid, Spinnrad GmbH) was added to 100 ml drinking water to give a solution of 30 000 ppm
n-Octyl-β-D-glucopyranoside: 4.62 ml of a 65% n-octyl-β-D-glucopyranoside solution (AG6202, Akzo Nobel) was added to 100 ml of drinking water to give a solution of 30000 ppm
Di-n-decyldimethyl ammonium chloride: 3.75 ml of a 40% di-n-decyldimethyl ammonium chloride solution (Acticide DDQ 40 solution, Thor Specialities UK Ltd) was added to 100 ml of drinking water to give a solution of 15000 ppm
ε-polylysine (PPL): 10 g of PPL was added to 100 ml of $H_2O$ to give a concentration of 100000 ppm Mixing Procedure:
Volumes of surfactant and PPL as indicated in the following Tables were added to glass flasks and adjusted to 100 ml with drinking water. Test mixtures were incubated at room temperature (~20° C.) and stored at room temperature for 24 hrs until quantification of particulate matter.

TABLE 24

Relative amounts of particulates in diluted mixtures of n-decyl-β-D-glucopyranoside and PPL.

| | ε-polylysine | | |
| --- | --- | --- | --- |
| n-Decyl-β-D-glucopyranoside | 500 µl (500 ppm) | 1000 µl (1000 ppm) | 3000 µl (3000 ppm) |
| 1000 µl (300 ppm) | ++ | +++ | +++ |
| 330 µl (100 ppm) | + | ++ | ++ |
| 100 µl (30 ppm) | + | ++ | ++ |

CMC of n-decyl-β-D-glucopyranoside ($H_2O$, 20° C.): approx. 330 ppm

TABLE 25

Relative amounts of particulates in diluted mixtures of n-octyl-β-D-glucopyranoside and PPL.

| | ε-polylysine | | |
|---|---|---|---|
| n-Octyl-β-D-glucopyranoside | 500 µl (500 ppm) | 1000 µl (1000 ppm) | 3000 µl (3000 ppm) |
| 5000 µl (1500 ppm) | ++ | ++ | ++ |
| 2500 µl (750 ppm) | + | + | + |
| 1000 µl (300 ppm) | + | + | ++ |

CMC of n-octyl-β-D-glucopyranoside (H$_2$O, 20° C.): 19 mM, approx. 2800 ppm

TABLE 26

Relative amounts of particulates in diluted mixtures of di-n-decyldimethyl ammonium chloride and PPL.

| | ε-polylysine | | |
|---|---|---|---|
| Di-n-decyldimethyl ammonium chloride | 500 µl (500 ppm) | 1000 µl (1000 ppm) | 3000 µl (3000 ppm) |
| 1000 µl (150 ppm) | − | − | − |
| 330 µl (50 ppm) | − | − | − |
| 100 µl (15 ppm) | − | − | − |

CMC of di-n-decyldimethyl ammonium chloride (H$_2$O, 20° C.): 1.5 mM, approx. 0.543 ppm when average molecular weight is 363.

EXAMPLE 17

A concentrated solution of non-ionic surfactant and nisin was freshly prepared as follows: 17.8 g of AG6210 was dissolved at room temperature in a final volume of 100 ml drinking water to give a final concentration of 100000 ppm. 2.5 g of nisin was dissolved into the above mixture to give a final concentration of 25000 ppm.

Test mixtures (50 ml) were prepared by diluting defined amounts of the concentrated solution with water to a final volume of 50 ml. Mixtures were stored at room temperature (~20° C.) for the time shown prior to quantification of particulate matter. Results are shown in Table 27.

TABLE 27

Relative amounts of particulates in diluted mixtures of AG6210 and nisin after varying incubation times. Dilution from concentrated solution of 100000 ppm AG6210 & 25000 ppm ε-polylysine

| | Crystals at timepoint/hrs | | | | |
|---|---|---|---|---|---|
| Dilution | 24 | 48 | 72 | 96 | 128 |
| 1:20 | + | ++ | ++ | ++ | ++ |
| 1:30 | + | + | ++ | ++ | ++ |
| 1:40 | + | + | ++ | ++ | ++ |
| 1:50 | + | ++ | ++ | ++ | ++ |
| 1:60 | + | ++ | ++ | ++ | ++ |
| 1:70 | + | ++ | + | ++ | ++ |
| 1:80 | + | ++ | + | + | ++ |
| 1:90 | + | ++ | ++ | ++ | ++ |
| 1:100 | + | ++ | ++ | ++ | ++ |
| 1:110 | + | ++ | ++ | ++ | ++ |
| 1:120 | + | + | ++ | ++ | ++ |
| 1:130 | + | + | ++ | ++ | ++ |
| 1:140 | + | + | ++ | ++ | ++ |
| 1:150 | + | + | + | ++ | ++ |
| 1:140 | + | + | ++ | ++ | ++ |
| 1:150 | + | + | + | ++ | ++ |

EXAMPLE 18

The antimicrobial efficacy of the following dilute ε-polylysine/AG6210 mixtures, prepared in accordance with the invention, was assessed as described above.

TABLE 28

Antimicrobial efficacy of dilute ε-polylysine/AG6210 mixtures prepared in accordance with the invention.

| ε-polylysine | | CFUs in each dilution of *E. coli* culture | | |
|---|---|---|---|---|
| (ppm) | AG 6210 | 1:1 | 1:10 | 1:100 |
| 250 | 1000 | ~40 | 0 | 0 |
| 500 | 2000 | 1 | 1 | 0 |
| 250 | 1000 | 0 | 1 | 0 |
| 125 | 500 | 40 | 25 | 0 |
| 83 | 333 | 80 | 40 | 20 |
| 250 | 0 | 100 | 40 | 25 |
| 0 | 1000 | >1000 | >1000 | >1000 |
| 0 | 0 | >1000 | >1000 | >1000 |

EXAMPLE 19

The following representative examples of antimicrobial liquid compositions have been prepared and shown to be antimicrobial.

| Substance | EINECS | CAS no. | % w/w |
|---|---|---|---|
| Didecyldimethyl-ammonium chloride | 230-525-2 | 7173-51-5 | <2 |
| Benzyl-C12-16-alkyldimethyl chlorides | 270-325-2 | 68424-85-1 | <2 |
| Decylglucoside | Surfactant | 54549-25-6 | <8 |
| C8 alkyl glucoside | Surfactant | 108081-06-7 | <6 |
| Polylysine | Surfactant | 28211-04-3 | <2 |
| Water | | | To make up to 100 |

| Substance | EINECS | CAS no. | % by weight |
|---|---|---|---|
| Didecyldimethyl-ammonium chloride | 230-525-2 | 7173-51-5 | <0.04 |
| Benzyl-C12-16-alkyldimethyl chlorides | 270-325-2 | 68424-85-1 | <0.02 |
| Decylglucoside | Surfactant | 54549-25-6 | <0.12 |
| Alkyl glucoside | Surfactant | 108081-06-7 | <0.08 |
| Polylysine | Surfactant | 28211-04-3 | <0.01 |
| Water | | | To make up to 100 |

The invention claimed is:

1. A method for preparing an antimicrobial preparation comprising crystalline particles of an antimicrobial agent, wherein said antimicrobial agent is an antimicrobial peptide selected from the group consisting of:

(i) a peptide of 10 to 30 amino acids having a net positive charge at or below physiological pH consisting of (a) lysine, arginine, glutamine and/or histidine and (b)

alanine, glycine, leucine, isoleucine, valine, methionine, proline, phenylalanine and/or tryptophan; and
(ii) epsilon-polylysine, polyarginine, and polyglutamine,
said method comprising:
(i) providing an aqueous liquid composition comprising said antimicrobial agent and at least one non-ionic surfactant in solution, wherein the non-ionic surfactant is present at a concentration above the critical micelle concentration (CMC) of the non-ionic surfactant in said composition, and
(ii) diluting said aqueous liquid composition with an amount of aqueous solvent sufficient to lower the concentration of the at least one non-ionic surfactant to a concentration at or below its CMC, thereby to result in the formation of crystalline particles of said antimicrobial agent and thereby to obtain a liquid preparation comprising said crystalline particles of said antimicrobial agent, and optionally
(iii) isolating at least a portion of said crystalline particles from said liquid preparation and/or removing at least a portion of the liquid phase of the liquid preparation to provide a more concentrated liquid preparation of crystalline particles.

2. The method of claim 1, wherein said at least one non-ionic surfactant is selected from the group consisting of polyoxyethylene glycol alkyl ethers, polyoxypropylene glycol alkyl ethers, glycoside alkyl ethers (alkyl (poly)glycosides), acyl-N-methyl glucamides, polyoxyethylene glycol octylphenol ethers, polyoxyethylene glycol alkylphenol ethers, glycerol alkyl esters, polyoxyethylene glycol sorbitan alkyl esters, sorbitan alkyl esters, cocamide MEA, cocamide DEA, dodecyldimethylamine oxide, block copolymers of polyethylene glycol and polypropylene glycol and polyethoxylated tallow amine (POEA).

3. The method of claim 1, wherein said at least one non-ionic surfactant is an alkyl (poly)glycoside represented by Formula I:

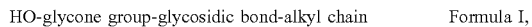

HO-glycone group-glycosidic bond-alkyl chain  Formula I,

4. The method of claim 3, wherein the glycone group of Formula I is a monosaccharide, disaccharide or trisaccariden or a sugar derivative thereof.

5. The method of claim 4, wherein said monosaccharide or one or more of the monosaccharide residues of the disaccharide or trisaccharide is a triose, a tetrose, a pentose, a hexose, a heptose, an octose, a nonose or a decose.

6. The method of claim 4, wherein said disaccharide is selected from the group consisting of acarviosin, allolactose, cellobiose, chitobiose, galactose-alpha-1,3-galactose, dentiobiose, isomalt, isomaltose, isomaltulose, kojibiose, lactitol, lactobionic acid, lactose, lactulose, laminaribiose, maltitol, maltose, mannobiose, melibiose, melibiulose, neohesperidose, nigerose, robinose, rutinose, sambubiose, sophorose, sucralose, sucrose, trehalose, turanose and xylobiose.

7. The method of claim 3, wherein said alkyl chain contains 4 to 20 carbon atoms.

8. The method of claim 3, wherein said alkyl chain is linear and/or saturated.

9. The method of claim 1, wherein said at least one non-ionic surfactant is selected from the group consisting of decyl glucoside, lauryl glucoside, octyl glucoside, decyl maltopyranoside, octyl maltopyranoside, octyl thioglucopyranoside, and n-heptyl thioglucopyranoside.

10. The method of claim 1, wherein said at least one non-ionic surfactant has a CMC of 0.1 mM to 50 mM.

11. The method of claim 1, wherein the aqueous liquid composition comprises at least two different non-ionic surfactants.

12. The method of claim 11, wherein said at least two different non-ionic surfactants are present in said liquid composition at a concentration above their CMC.

13. The method of claim 12, wherein at least one of the at least two different non-ionic surfactants is not diluted to a concentration at or below its CMC.

14. The method of claim 1, wherein the aqueous liquid composition comprises decyl glucoside and octyl glucoside in a w/w percentage ratio of 35-45% octyl glucoside and 65-55% decyl glucoside.

15. The method of claim 14, wherein the liquid preparation of step (ii) contains the antimicrobial agent at a concentration of 750 ppm to 1250 ppm and the combination of octyl glucoside and decyl glucoside at a total concentration of 750 ppm to 1250 ppm.

16. The method of claim 1, wherein the aqueous liquid composition further contains an anionic, cationic or zwitterionic surfactant selected from the group consisting of cetyl trimethylammonium bromide, cetyl trimethylammonium chloride, benzalkonium chloride, benzethonium chloride cetalkonium chloride, cetylpyridinium chloride, cetrimonium, didecyldimethylammonium chloride, dioctadecyldimethylammonium bromide and domiphen bromide.

17. The method of claim 1, wherein said antimicrobial agent is ε-polylysine and said at least one non-ionic surfactant is octyl glucoside, decyl glucoside, or a mixture of octyl glucoside and decyl glucoside.

18. An antimicrobial preparation obtained or obtainable from the method of claim 1.

19. A method for combating contamination of a site with a microorganism, said method comprising contacting the site and/or the microorganism with a crystalline particle of the antimicrobial preparation of claim 1.

20. The method of claim 19, wherein the microorganism is on a surface selected from surfaces of food or drink processing, preparation, storage or dispensing machinery or equipment, meat processing machinery or equipment, abattoir machinery or equipment, and fruit and vegetable processing machinery or equipment, surfaces of air conditioning apparatus, surfaces of industrial machinery, surfaces of storage tanks, surfaces of medical or surgical equipment, surfaces of aquatic/marine equipment, the surfaces of buildings and other structures or the surfaces of food.

21. The method of claim 19, wherein the microorganism is in a material selected from the group consisting of clinical/scientific waste, animal or human food stuffs, personal hygiene products, cosmetics, soil, drinking water supplies, waste water supplies, agricultural feedstuffs, agricultural water supplies, insecticide formulations, pesticide formulations, herbicide formulations, industrial lubricants, cell and tissue culture media, and cell and tissue cultures.

22. The method of claim 19, wherein the microorganism or the microbial infection is in or on an internal or external body surface, a body tissue or a body fluid.

23. The method of claim 9, wherein said at least one nonionic surfactant is selected from the group consisting of octyl beta-D-glucopyranoside and decyl beta-D-glucopyranoside.

24. The method of claim 19, wherein the microorganism is in a material selected from meat, fish, vegetables and fruit.

* * * * *